(12) United States Patent
Wu et al.

(10) Patent No.: US 11,766,350 B2
(45) Date of Patent: Sep. 26, 2023

(54) METHOD AND APPARATUS FOR A PASSIVE KNEE JOINT

(71) Applicant: The Regents of the University of California, Oakland, CA (US)

(72) Inventors: Shangli Wu, Santa Clara, CA (US); Homayoon Kazerooni, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/156,702

(22) Filed: Oct. 10, 2018

(65) Prior Publication Data
US 2019/0105190 A1 Apr. 11, 2019

Related U.S. Application Data

(60) Provisional application No. 62/570,563, filed on Oct. 10, 2017.

(51) Int. Cl.
*A61F 5/01* (2006.01)
*B25J 9/00* (2006.01)
(Continued)

(52) U.S. Cl.
CPC ............ *A61F 5/0125* (2013.01); *A61F 2/644* (2013.01); *A61F 5/0123* (2013.01); *A61H 1/024* (2013.01);
(Continued)

(58) Field of Classification Search
CPC ........ A61F 5/01; A61F 5/0102; A61F 5/0123; A61F 5/0125; A61F 5/0127; A61F 5/058;
(Continued)

(56) References Cited

U.S. PATENT DOCUMENTS 4,310,932 A * 1/1982 Nader .................... A61F 2/644
623/45
4,911,709 A * 3/1990 Marlow .................. A61F 2/644
623/46
(Continued)

FOREIGN PATENT DOCUMENTS

GB 661131 A 11/1951
GB 2181352 A * 4/1987 ............... A61F 2/64
(Continued)

OTHER PUBLICATIONS

Shank. Merriam Webster's Online Dictionary, p. 2 definition 1a. https://www.merriam-webster.com/dictionary/shank (Year: 2018).*
(Continued)

*Primary Examiner* — Rachael E Bredefeld
*Assistant Examiner* — Trisha Talapatra
(74) *Attorney, Agent, or Firm* — Sterne, Kessler, Goldstein & Fox P.L.L.C.

(57) ABSTRACT

An artificial knee is configured to be worn by a person. Artificial knees include a thigh link configured to move in unison with a thigh of the person, and a shank link configured to be coupled to the thigh link. Artificial knees include a compression spring coupled to the thigh link at a first end of the compression spring, the compression spring configured to be coupled to the shank link at a second end of the compression spring. The compression spring is configured to provide an extension torque between the thigh link and the shank link during a first range of motion of the thigh link and the shank link relative to each other. The compression spring is configured to provide a flexion torque between the thigh link and the shank link during a second range of motion of the thigh link and the shank link relative to each other.

18 Claims, 29 Drawing Sheets

(51) Int. Cl.
    *A61H 1/02*    (2006.01)
    *A61H 3/00*    (2006.01)
    *A61F 2/64*    (2006.01)
    *A61F 2/50*    (2006.01)

(52) U.S. Cl.
    CPC ............. *A61H 1/0244* (2013.01); *A61H 3/00* (2013.01); *B25J 9/0006* (2013.01); *A61F 2002/5043* (2013.01); *A61F 2002/5072* (2013.01); *A61F 2002/5079* (2013.01); *A61F 2005/0165* (2013.01); *A61F 2005/0179* (2013.01); *A61H 2201/0192* (2013.01); *A61H 2201/164* (2013.01); *A61H 2201/165* (2013.01); *A61H 2201/1642* (2013.01); *A61H 2201/1671* (2013.01); *A61H 2201/5007* (2013.01); *A61H 2201/5053* (2013.01); *A61H 2201/5069* (2013.01); *A61H 2203/0406* (2013.01); *A61H 2205/10* (2013.01); *A61H 2205/102* (2013.01); *A61H 2205/12* (2013.01)

(58) Field of Classification Search
    CPC ................ A61F 5/05825; A61F 5/0585; A61F 2005/0132; A61F 2005/0134; A61F 2005/0137; A61F 2005/0141; A61F 2005/0144; A61F 2005/0146; A61F 2005/0148; A61F 2005/0151; A61F 2005/0153; A61F 2005/0155; A61F 2/644; A61F 2/604; A61F 2/642; A61F 2/64; A61F 2005/0165; A61F 2005/0169; A61F 2005/0179; B25J 9/0006; A41D 13/05; A41D 13/0543; A41D 13/06; A41D 13/065; A63B 23/04

See application file for complete search history.

(56) References Cited

U.S. PATENT DOCUMENTS

| | | | |
|---|---|---|---|
| 8,313,534 | B1* | 11/2012 | Chen ................... A61F 2/644 623/43 |
| 2003/0093018 | A1 | 5/2003 | Albrecht et al. |
| 2006/0260620 | A1* | 11/2006 | Kazerooni ........... A61B 5/6829 128/845 |
| 2015/0005686 | A1* | 1/2015 | Kazerounian ......... A61F 5/0123 602/16 |
| 2016/0324665 | A1* | 11/2016 | Boiten .................... A61F 2/642 |
| 2016/0374887 | A1 | 12/2016 | Wu et al. |
| 2018/0055673 | A1* | 3/2018 | Humphrey ............ A61F 5/0125 |
| 2018/0243120 | A1 | 8/2018 | Wu et al. |

FOREIGN PATENT DOCUMENTS

| | | |
|---|---|---|
| WO | 2017050552 A1 | 3/2017 |
| WO | 2019075080 A1 | 4/2019 |

OTHER PUBLICATIONS

Thoughtco. Calculating Torque with Examples, p. 1. https://www.thoughtco.com/calculating-torque-2698804 (Year: 2018).*

MW Components. Compression Springs, p. 1. https://www.mwcomponents.com/compression-springs (Year: 2022).*

"Int'l Application Serial No. PCT/US18/55234, Int'l Search report and Written Opinion dated Feb. 3, 2019", 12 pgs.

* cited by examiner $\theta_{KNEE} = \theta_{START}$ $\theta_{KNEE} = \theta_{ENG}$ $\theta_{KNEE} = \theta_{TOG}$ $\theta_{KNEE} = \theta_{REL}$ $\theta_{KNEE} = \theta_{END}$

METHOD AND APPARATUS FOR A PASSIVE KNEE JOINT

CROSS-REFERENCE TO RELATED APPLICATIONS

This application claims the benefit under 35 U.S.C. § 119(e) of U.S. Provisional Patent Application No. 62/570,563, filed on Oct. 10, 2017, which is incorporated by reference herein in its entirety for all purposes.

TECHNICAL FIELD

This disclosure generally relates to artificial lower limb prosthetics and orthotic systems, and more particularly, to an exoskeleton knee that can be used for a variety of orthotic applications.

BACKGROUND

A traditional knee-ankle-foot orthosis (KAFO) is used to increase the patient stability during the weight-bearing phase of walking. A traditional KAFO locks the knee in full extension, which provides stability. This locked posture results in patients' ability to ambulate with gait deviations that can lead to overuse injuries. A stance control orthosis (SCO) allows the knee to flex during the swing phase of the gait cycle and prevents knee flexion for stability during the stance phase. By allowing the knee to bend during the swing phase, SCOs allow a more natural gait, which may reduce secondary complications from gait compensations and allow the patient to walk with less effort.

Fillauer describes a gravity-actuated knee joint locking system for its Swing Phase Lock (SPL) orthosis (U.S. Patent20030153854). A Swing Phase Lock uses an internal pendulum mechanism mounted on the thigh link (the member that moves in unison with the user's thigh). As the thigh link moves, the pendulum swinging motion locks and unlocks the shank link (the member that moves in unison with the user's shank) relative to the thigh link. This allows for locking and unlocking of the knee joint for appropriate phases of a walking cycle.

Free Walk orthosis (marketed by OTTOBOCK) and UTX orthosis (marketed by Becker) work based on the principle. The dorsiflexion of the foot at the end of the stance pulls on a controllable cable connected to a locking mechanism at the knee joint. This pulling action disengages the locking mechanism for swing. The locking mechanism is spring loaded and locks the knee when the knee is fully extended.

Sensor Walk (manufactured by OTTOBOCK) uses a wrap spring at the knee joint for locking and unlocking the knee. This orthosis includes two sets of sensors: one at the knee to measure the knee angle; and another at the footplate to measure force between the foot and the floor. The orthosis also includes a wrap spring clutch replacing the lateral knee joint to provide braking capability to support the anatomic knee joint, a microprocessor-controlled release for the brake, and a battery pack carried in a waist pack. Sensors in the footplate disengage the wrap spring clutch and allow the knee to bend in the late stance phase when weight has been transferred to the contralateral side and is ready for single-limb support. A knee sensor senses extension of the knee after toe off and sends a signal to the microprocessor putting the wrap spring clutch in its locked position.

Horton Stance Control Orthosis (U.S. Pat. No. 6,635,024 and U.S. 200220169402) includes a locking mechanism that locks and unlocks the knee with the help of a push rod. The push rod is placed between the heel and the knee. The push rod locks the knee at heel strike and unlocks the knee right at the end of stance phase. The device locks knee at any angle.

DESCRIPTION OF EMBODIMENTS

Figure 1:
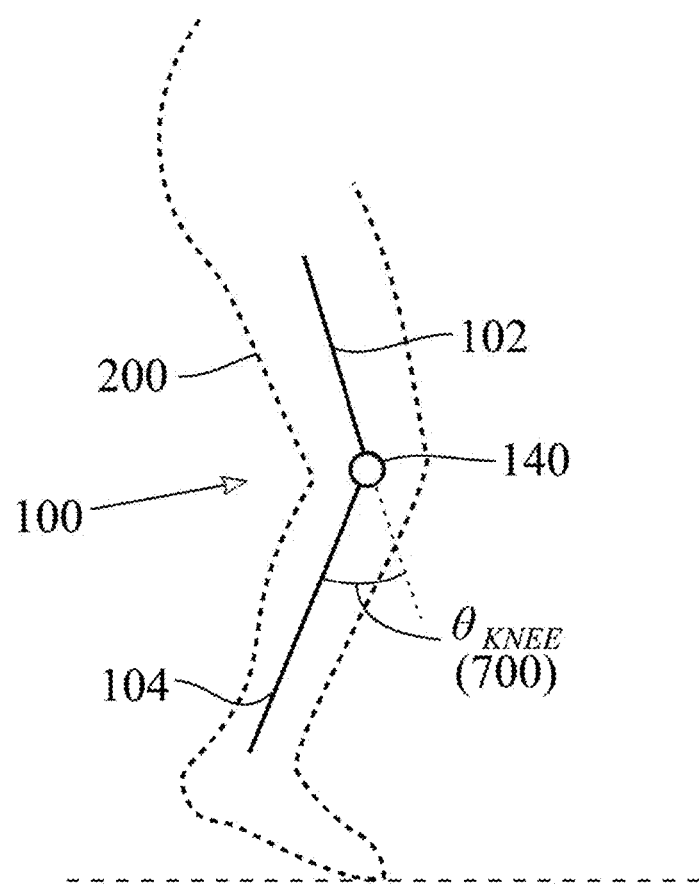
FIG. 1 depicts an embodiment of an artificial knee 100 associate with person 200, configured in accordance with various embodiments.

FIG. 1 depicts an embodiment of an artificial knee 100 associate with person 200, configured in accordance with various embodiments. Knee angle $\theta_{KNEE}$ 700 is defined as an angle between the extension of human thigh relative to the human shank as shown in FIG. 1. In various embodiments, the human knee is considered extending if knee angle $\theta_{KNEE}$ 700 gets smaller or is reduced. In some embodiments, the human knee is considered flexing if knee angle $\theta_{KNEE}$ 700 gets larger or is increased. Accordingly "knee extension" or "extending the knee" refer to the situations where the human leg intends to straighten. Similarly, "knee flexion" or "flexing the knee" refer to the situations where the human leg intends to bend.

Figure 2:
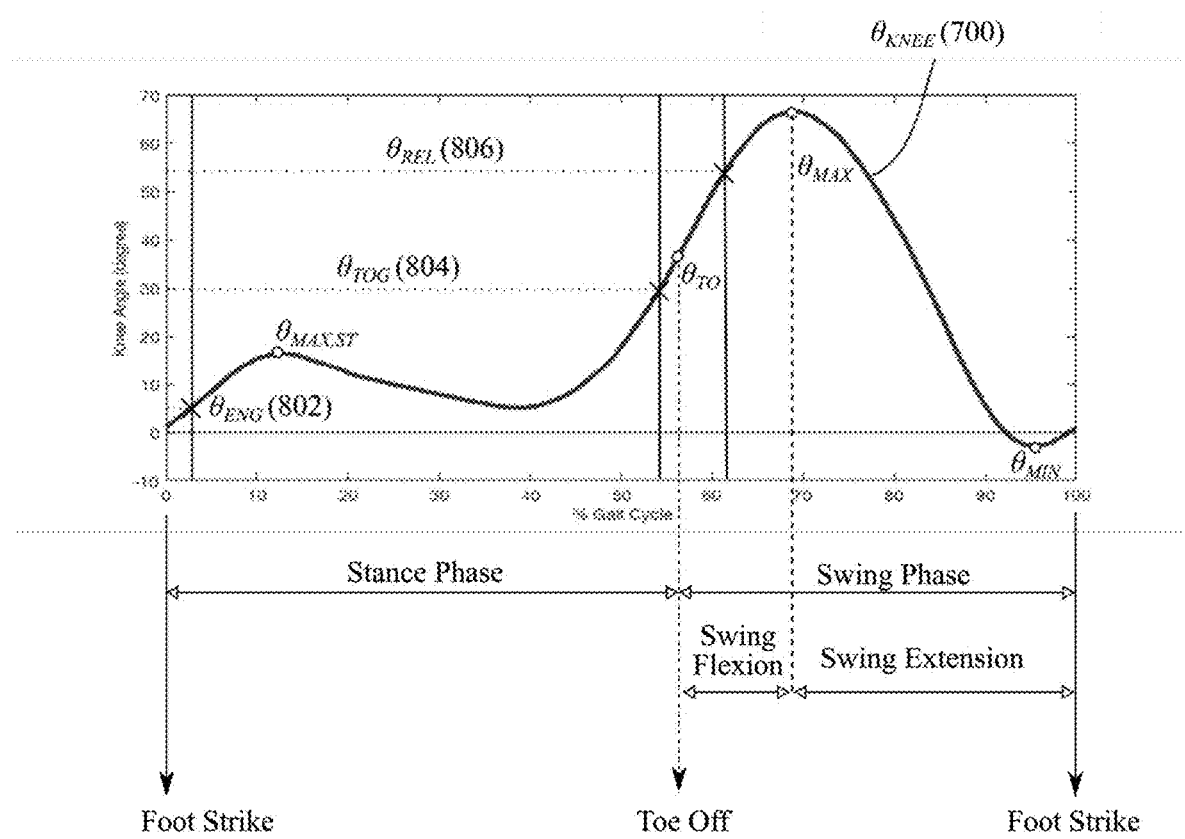
FIG. 2 depicts knee angle $\theta_{KNEE}$ 700 during a walking cycle, implemented in accordance with various embodiments.

FIG. 2 depicts knee angle $\theta_{KNEE}$ 700 during a walking cycle, implemented in accordance with various embodiments. As illustrated in FIG. 2, there are two main phases in a gait cycle, a stance phase and a swing phase. The stance phase refers to configurations when a foot is on the ground, and the swing phase refers to configurations when the foot is off the ground. The swing phase can be subdivided into two phases: swing flexion—when the knee flexes, and swing extension—when the knee extends. In some embodiments, the gait cycle starts at foot strike. Later, the human leg enters the swing phase at toe off. In some embodiments, the swing phase starts with a swing flexion phase, followed by the swing extension phase. As can be seen in FIG. 2, knee angle $\theta_{KNEE}$ 700, during the entire walking cycle, flexes to local minimums twice: once during the stance phase and once during the swing phase. During the stance phase knee angle $\theta_{KNEE}$ 700 increases (flexes) to $\theta_{MAX,ST}$. During the swing phase, knee angle $\theta_{KNEE}$ 700 reaches maximum knee flexion $\theta_{MAX}$. $\theta_{TO}$ represents knee angle $\theta_{KNEE}$ 700 at toe off. The knee reaches the minimum knee angle $\theta_{MIN}$ toward the end of the swing phase. Although there are variations from the plot shown in FIG. 2, the human knee generally goes through two flexions in a walking cycle: a small flexion during the stance phase and a large flexion during the swing phase. The small flexion is in response to the person's weight shifting, while the larger flexion provides toe clearance during the swing phase.

Various embodiments disclosed herein provide artificial knee 100 (which may be either a prosthetic knee or an orthotic knee) which is configured to exhibit the behavior of a human knee without the implementation of actuators, sensors, and computers. Such configurations of artificial knee 100 provide a low cost implementation of an artificial knee for various orthotic, prosthetic, and exoskeleton applications. Referring back to FIG. 1, artificial knee 100 includes thigh link 102 and shank link 104, which are rotatably coupled to each other at knee joint 140. Configurations of artificial knee 100 disclosed herein, and described above with reference to FIG. 1 and FIG. 2, are configured to resist knee flexion during the stance phase. Accordingly, artificial knee 100 helps a human user during the stance phase to support a portion of the user's weight. Such configurations of artificial knee 100 are also configured to encourage and/or facilitate knee flexion during the swing phase to assist in toe clearance during the swing flexion phase. Such configurations of artificial knee 100 are also configured to allow free swing extension in the swing extension phase.

The above three features provide artificial knee 100 with the ability to support the user during the stance phase, but remain free during the swing extension. Such configurations further encourage the knee flexion at an early portion of the swing phase. As will be discussed in greater detail below, all of the above features are achieved passively without the use of actuators, computers and sensors.

As discussed above, artificial knee 100 is configured to produce an extension torque from engagement angle 802 (represented by $\theta_{ENG}$ 802 in FIG. 2) to toggle angle 804 (represented by $\theta_{TOG}$ 804 in FIG. 2). Accordingly, artificial knee 100 resists flexion and assists the user during the stance phase to support at least a portion of the user's weight. Extension torque is defined as a torque that causes artificial knee 100 to extend. Artificial knee 100 further provides flexion torque from toggle angle $\theta_{TOG}$ 804 to a release angle 806 represented by $\theta_{REL}$ 806 in FIG. 2. This means artificial knee 100 encourages knee flexion during the swing phase to assist in toe clearance. Flexion torque is defined as a torque that causes artificial knee 100 to flex. As discussed above with reference to FIG. 1, flexion torque is a torque that causes knee angle $\theta_{KNEE}$ 700 to increase. $\theta_{TOG}$ 804 represents a particular knee angle at which torque in artificial knee 100 switches (toggles) from an extension torque to a flexion torque. The extension torque is utilized to support weight, such as a user's weight, while the flexion torque is utilized to clear the ground. Once the knee has accomplished the above two features, it then freely extends and prepares for a foot strike, as shown in FIG. 2. In this way, the mechanism that created an extension torque between $\theta_{ENG}$ 802 and $\theta_{TOG}$ 804, and a flexion torque between $\theta_{TOG}$ 804 and $\theta_{REL}$ 806, becomes ineffective when the knee is extending before foot strike. Accordingly, artificial knee 100 first provides an extension torque from engagement angle $\theta_{ENG}$ 802 to toggle angle $\theta_{TOG}$ 804, and then provides a flexion torque from toggle angle $\theta_{TOG}$ 804 to release angle $\theta_{REL}$ 806. In various embodiments, artificial knee 100 does not need to provide any other torque in any other phases of the knee trajectory. In various embodiments, the state when artificial knee 100 provides an extension torque is called an "extension support state". Furthermore, the state when artificial knee 100 provides a flexion torque is called a "flexion support state".

In various embodiments, artificial knee 100 may have designated angles $\theta_{ENG}$ 802, $\theta_{TOG}$ 804, $\theta_{REL}$ 806. $\theta_{ENG}$ 802, $\theta_{TOG}$ 804, and $\theta_{REL}$ 806 which are configured to determine when the extension torque begins, when the extension torque switches to flexion torque, and when the flexion torque ends. In various embodiments, the range limits of angles $\theta_{ENG}$ 802, $\theta_{TOG}$ 804, and $\theta_{REL}$ 806 are determined based on equations 1, 2, and 3 shown below:

$$\theta_{MIN} < \theta_{ENG} < \theta_{MAX,ST} \quad (1)$$

$$\theta_{MAX,ST} < \theta_{TOG} < \theta_{TO} \quad (2)$$

$$\theta_{TO} < \theta_{REL} < \theta_{MAX} \quad (3)$$

As shown in FIG. 2, $\theta_{MIN}$ is a minimum knee angle during the gait, $\theta_{MAX,ST}$ is a maximum knee angle in the stance phase, $\theta_{TO}$ is the knee angle at toe off, and $\theta_{MAX}$ is the maximum knee angle throughout the gait.

If $\theta_{ENG} > \theta_{MAX,ST}$, artificial knee 100 is configured to provide little to no resistance during a portion of stance phase. If $\theta_{REL} < \theta_{TO}$, artificial knee 100 is configured to not encourage or facilitate toe clearance. In various embodiments, $\theta_{TOG}$ 804 is configured to be the same as knee angle $\theta_{KNEE}$ 700 at toe off so that flexion torque is generated as soon as toe off occurs. To prevent generation of extension torque after toe off, as such extension torque may hinder knee flexion, $\theta_{TOG}$ 804 is configured to be smaller than the average knee angle $\theta_{KNEE}$ 700 at toe off. As discussed above, extension torque generated after toe off may prevent knee flexion utilized for ground clearance. In various embodiments, the average minimum knee angle at toe off is approximately 35 degrees. Therefore, according to some embodiments, $\theta_{TOG}$ 804 is configured to be 30 degrees. Such a configuration of $\theta_{TOG}$ 804 ensures that the toggle point of artificial knee 100 occurs before the toe off. Various other values of $\theta_{TOG}$ 804 may be configured and implemented depending on the applications and other criteria associated with a user. In some embodiments, $\theta_{ENG}$ 802 is configured to be small, and OR, 806 is configured to be large to generate more supportive torque. However, in various embodiments, $\theta_{REL}$ 806—$\theta_{ENG}$ 802 is configured to remain within the range of normal human knee operation. As shown in equation 4:

$$(\theta_{REL} - \theta_{ENG}) < (\theta_{MAX} - \theta_{MIN}) \quad (4)$$

In some embodiments, $\theta_{MIN}$, $\theta_{MAX,ST}$ and $\theta_{MAX}$ are configured to be about 0, 20, and 65 degrees, respectively. In view of various gaits for different individuals and users, in some embodiments, artificial knee 100 is configured such that $\theta_{ENG}$ 802 and $\theta_{REL}$ 806 are about 5 and 55 degrees, respectively. As similarly discussed above, other values for $\theta_{ENG}$ 802 and $\theta_{REL}$ 806 may be implemented depending on particular applications and criteria associated with a user.

Figure 3:
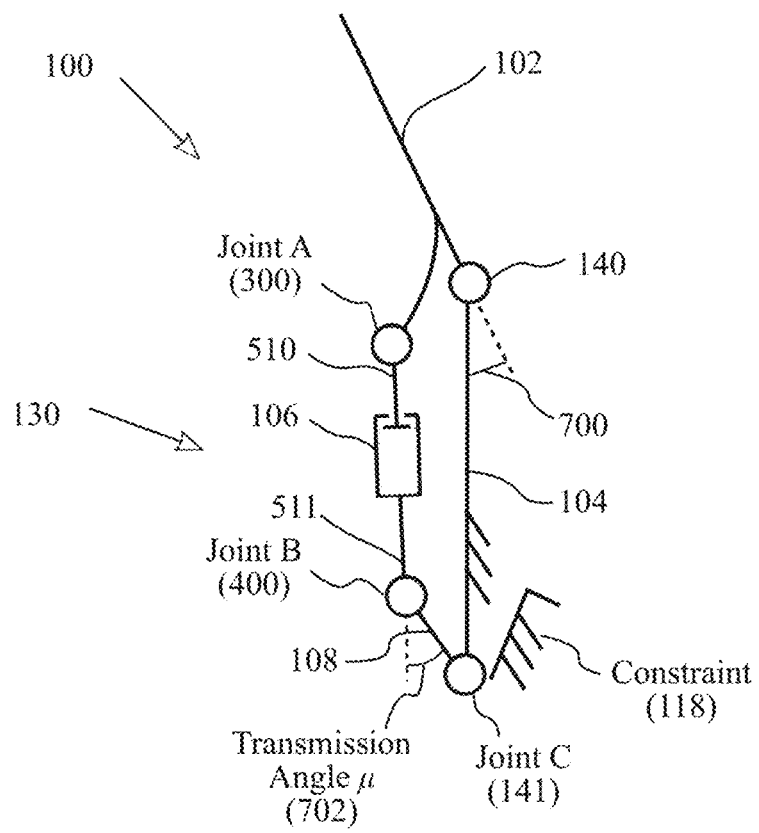
FIG. 3 depicts an embodiment of artificial knee 100, configured in accordance with various embodiments.
Figure 26:
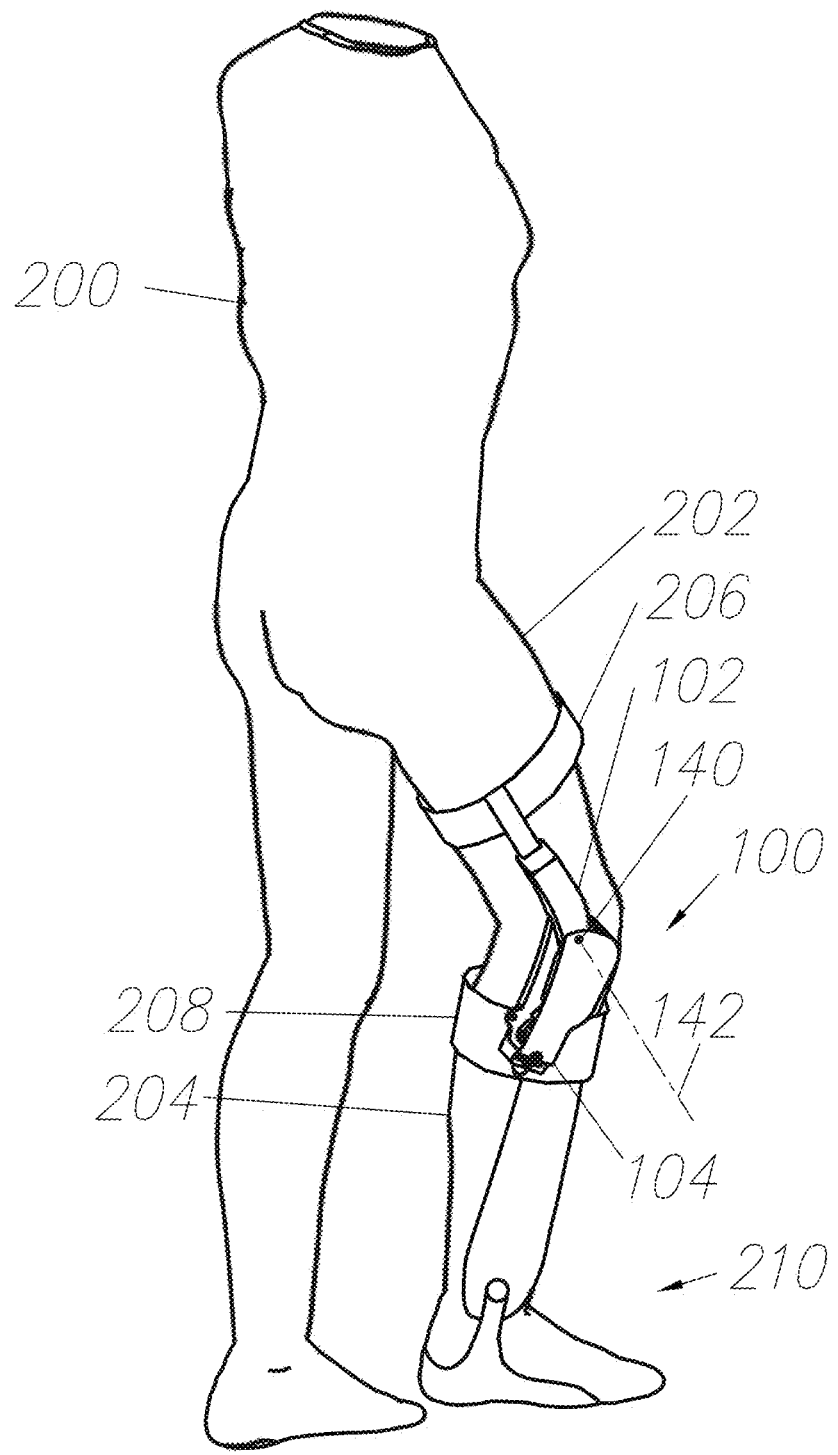
FIG. 26 depicts an embodiment of artificial knee 100 worn by person 200 as an orthotics knee, configured in accordance with various embodiments.
Figure 27:
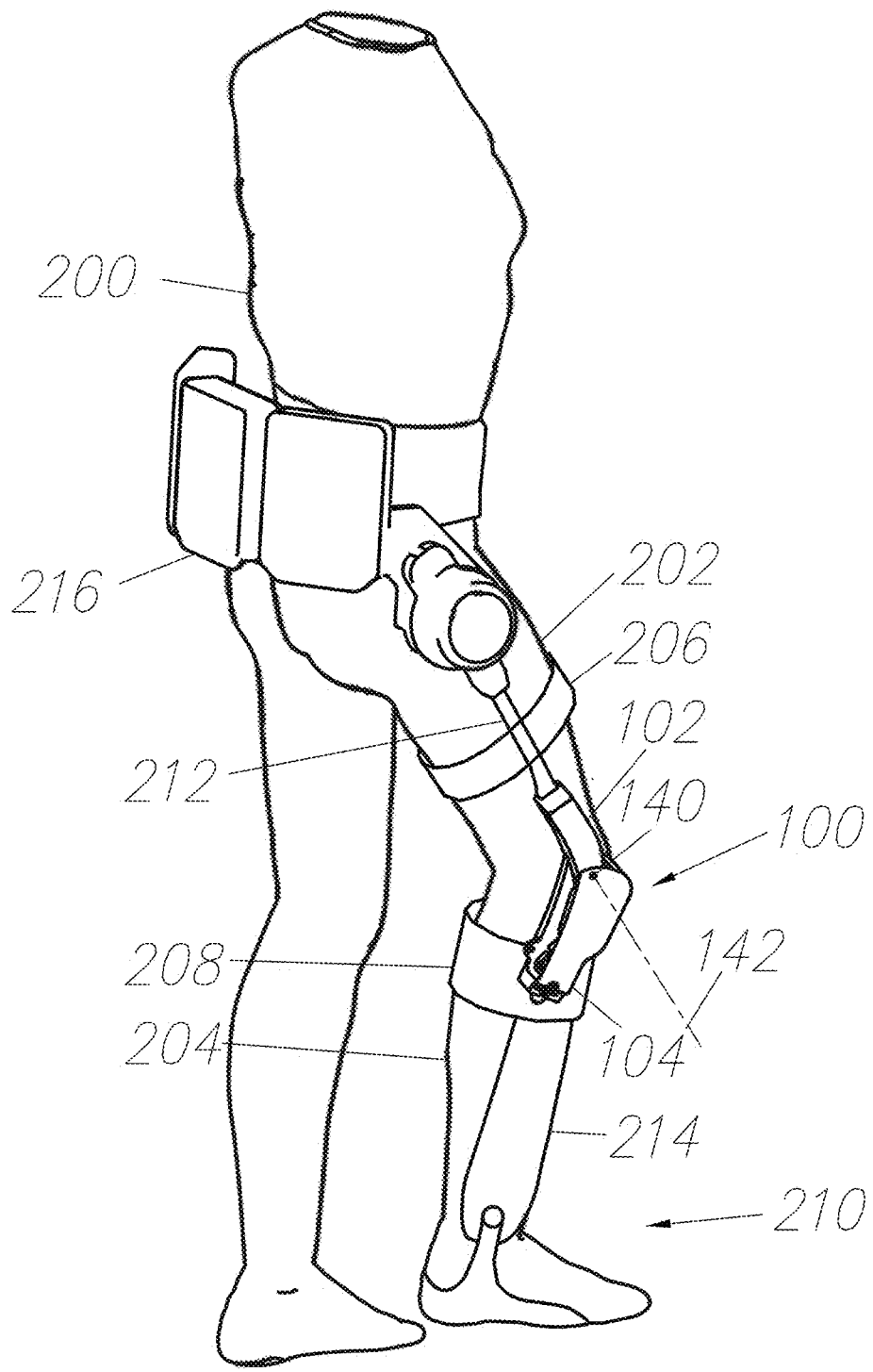
FIG. 27 depicts an embodiment of artificial knee 100 worn by person 200 as an exoskeleton knee, configured in accordance with various embodiments.

FIG. 3 depicts an embodiment of artificial knee 100, configured in accordance with various embodiments. Artificial knee 100 comprises thigh link 102, and shank link 104 rotating about knee joint 140. Knee angle $\theta_{KNEE}$ 700 represents the angle between shank link 104 and the extension of thigh link 102. Since in orthotic and prosthetic applications, the human knee angle and the artificial knee angle coincide on each other, knee angle $\theta_{KNEE}$ 700 is used to represent both the angle of human knee and the angle of artificial knee 100. In some embodiments, which may be implemented as exoskeletons or orthotic systems, thigh link 102 and shank link 104 are configured to move in unison with the human's thigh and shank. As will be discussed in greater detail below, thigh brace 206 shown in FIG. 26 and FIG. 27, is used to couple thigh link 102 to person's thigh. As will also be discussed in greater detail below, as shown in FIG. 26 and FIG. 27, shank brace 208 is used to couple shank link 104 to person's shank.

FIG. 3 shows that artificial knee 100 further includes compression spring 106 rotatably coupled to thigh link 102 from first end 510. Artificial knee 100 further includes fourth link 108 rotatably coupled with second end 511 of compression spring 106. Compression spring 106, fourth link 108, as well as shank link 104 and thigh link 102, form four bar linkage 130 as shown in FIG. 3. Additional details of four bar linkage 130 and its features and functionality are provided below.

In various embodiments, thigh link 102 and shank link 104 are configured as a driver link and a ground link of four bar linkage 130 respectively. Further, compression spring 106 and fourth link 108 are configured as a coupler link and a follower link of four bar linkage 130. Transmission angle μ 702 is defined as the angle between fourth link 108 and compression spring 106 as shown in FIG. 3. When compression spring 106 is not compressed and acts like a rigid link, four bar linkage 130 is configured as a rocker-rocker four-bar linkage, which means that both driver link (thigh link 102) and follower link (fourth link 108) have reciprocating motion. Constraint 118 is coupled to shank link 104 to stop the rotation of fourth link 108 (follower link) at a designated angle. In some embodiments, constraint 118 is a hard stop formed on shank link 104. In various embodiments, constraint 118 is parallel with fourth link 108 when it blocks fourth link 108. The range of motion of the thigh link 102 (the driver link of four bar linkage 130 as discussed above) is defined by the singular points where compression spring 106 (the coupler link for four bar linkage 130) aligns with fourth link 108. In some embodiments, this may be where transmission angle μ 702 is 0.

Figure 4A:
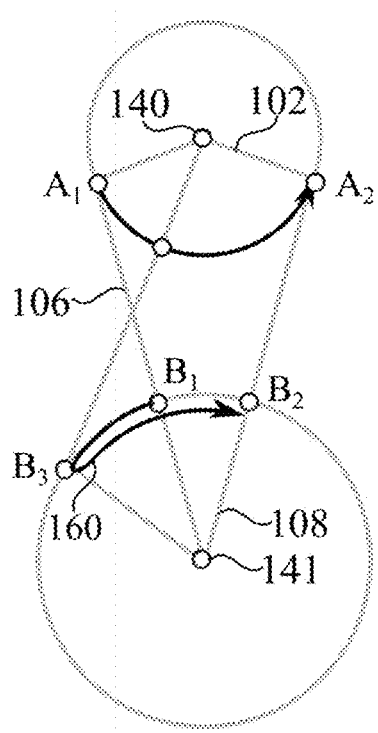
FIG. 4A, FIG. 4B, FIG. 4C, and FIG. 4D depict thigh link 102 moving from one singular point to another, implemented in accordance with various embodiments.
Figure 4B:
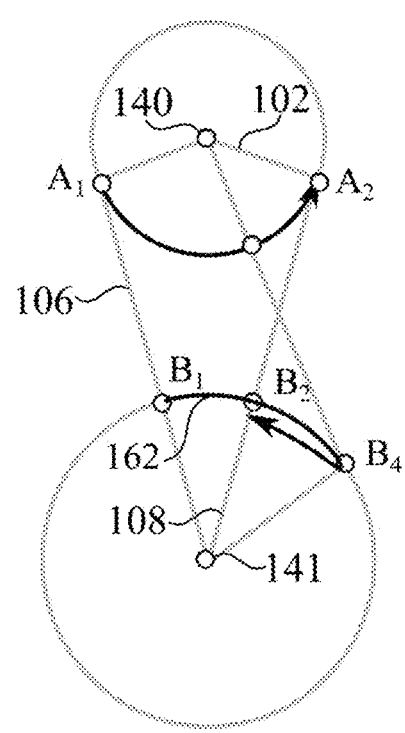
Figure 4C:
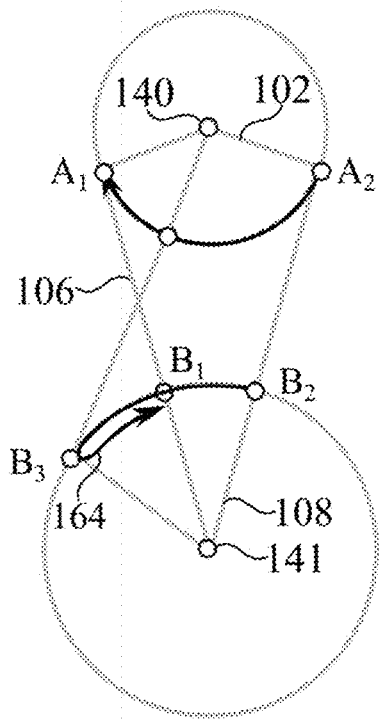
Figure 4D:
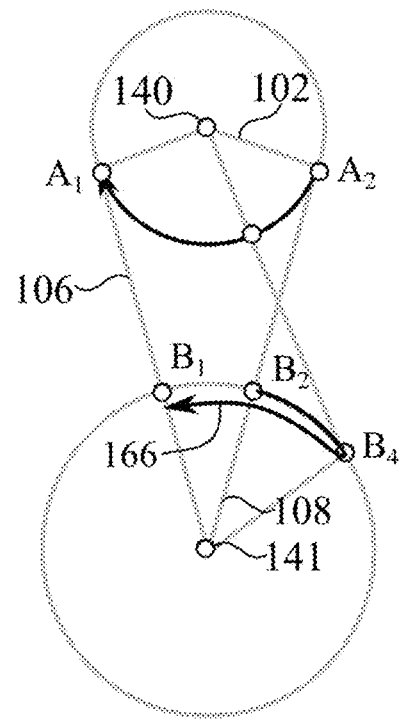

FIG. 4A, FIG. 4B, FIG. 4C, and FIG. 4D depict thigh link 102 moving from one singular point to another, implemented in accordance with various embodiments. FIG. 4A shows artificial knee 100 when thigh link 102 moves from one singular configuration $A_1$ to another singular configuration $A_2$. At each singular configuration, fourth link 108 has two available pathways or trajectories: it can follow trajectory 160 in FIG. 4A or follow trajectory 162 shown in FIG. 4B. In various embodiments, singular configurations are points where fourth link 108 has these two available trajectories. FIG. 4A and FIG. 4B show configurations where thigh link 102 moves from $A_1$ counter-clockwise to $A_2$. In some embodiments, fourth link 108 is initially located at singular point $B_1$. If fourth link 108 is perturbed to start moving anti-clockwise as shown in FIG. 4A, then trajectory 160 illustrates how fourth link 108 moves from $B_1$ to $B_2$. FIG. 4B similarly shows thigh link 102 moving from $A_1$ to $A_2$. However, in this example, fourth link 108 is initially perturbed in a clockwise direction where it moves from $B_1$ to $B_2$ along trajectory 162. FIG. 4C and FIG. 4D show configurations where thigh link 102 moves clockwise from $A_2$ to $A_1$. In various embodiments, fourth link 108 is initially located at singular point $B_2$. If fourth link 108 is perturbed to start moving counter-clockwise as shown in FIG. 4C, then trajectory 164 shows how fourth link 108 moves from $B_2$ to $B_1$. FIG. 4D similarly shows thigh link 102 moving from $A_2$ to $A_1$ in a clockwise direction. However, in this example, fourth link 108 is initially perturbed in a clockwise direction where it moves from $B_2$ to $B_1$ along trajectory 166.

As illustrated in the examples set forth by FIGS. 4B and 4C, the operation of four bar linkage 130 is shown when follower link 108 is perturbed to travel along trajectory 162 when thigh link 102 travels from $A_1$ to $A_2$, and along trajectory 164 when thigh link 102 travels back from $A_2$ to $A_1$. As shown in FIG. 4B, fourth link 108 is perturbed to move along trajectory 162 at point $B_1$. While thigh link 102 moves from $A_1$ to $A_2$ in a counter-clockwise direction, fourth link 108 (the follower link) moves from $B_1$ to $B_2$ and to $B_4$, and then back to $B_2$ along trajectory 162. If fourth link 108 is perturbed to go along trajectory 164 (as shown in FIG. 4C), then fourth link 108 moves from $B_2$ to $B_1$ and to $B_3$ and then back to $B_2$ along trajectory 164, as is the case when thigh link 102 moves from $A_2$ to $A_1$ in a clockwise direction. Accordingly, FIG. 4B and FIG. 4C illustrate how four bar linkage 130 operates for an entire cycle of thigh link 102 if fourth link 108 is perturbed at point $B_1$ and $B_2$ along trajectories 162 and 164.

Figure 5A:
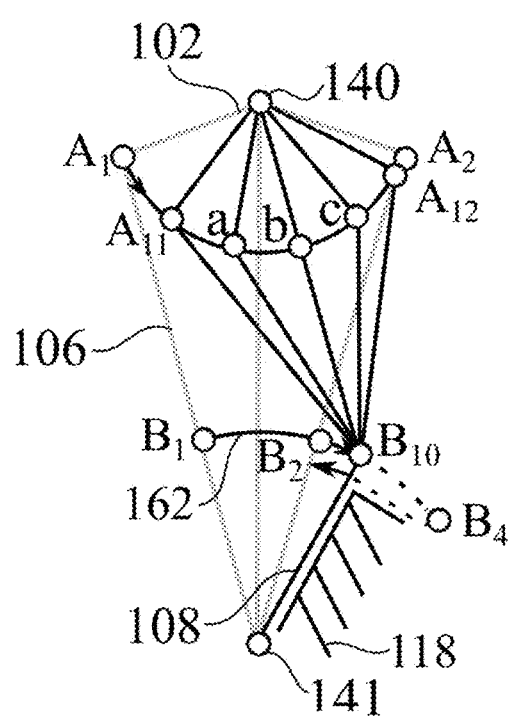
FIG. 5A and FIG. 5B depict artificial knee 100 providing support from a first singular point to a second singular point, while not providing support from the second singular point to the first singular point, implemented in accordance with various embodiments.
Figure 5B:
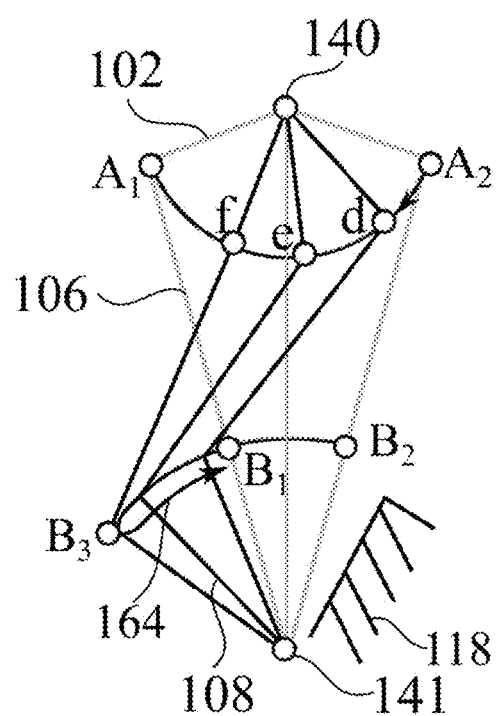

In various embodiments, constraint 118 is implemented and configured to block fourth link 108 between $B_2$ and $B_4$. Accordingly, FIG. 5A and FIG. 5B depict artificial knee 100 providing support from a first singular point to a second singular point, while not providing support from the second singular point to the first singular point, implemented in accordance with various embodiments. More specifically, FIG. 5A depicts artificial knee 100 when thigh link 102 rotates counter-clockwise from $A_1$ to $A_2$. FIG. 5B depicts artificial knee 100 when thigh link 102 rotates clockwise from $A_2$ to $A_1$. When thigh link 102 moves from $A_1$ to $A_2$ in a counter-clockwise direction (as shown in FIG. 5A), constraint 118 blocks fourth link 108. $B_{10}$ represents joint B when fourth link 108 (the follower link) becomes constrained. Similarly, $A_1$ represents joint A when fourth link 108 (the follower link) becomes constrained. Since coupler link (compression spring 106) is compressible, as thigh link 102 continues to move in a clockwise direction, coupler link (compression spring 106) gets compressed and resists the rotation of thigh link 102 relative to shank link 104. Points a, b, and c represent the locations of joint A when thigh link 102 travels from $A_{11}$ to $A_{12}$ while fourth link 108 (the follower link) is not moving. When thigh link travels from A12 to A2, fourth link 108 (the follower link) travels from $B_{10}$ to $B_2$. A small torque applied on fourth link 108, when fourth link 108 is at $B_2$, pushes fourth link 108 away from constraint 118. At this time, when thigh link 102 moves from $A_2$ in a clockwise direction (as shown in FIG. 5B), fourth link 108 moves along trajectory 164 with no constraint as shown in FIG. 5B. In this way, thigh link 102 moves from $A_2$ to $A_1$ through points d, e, and f with no resistance from compression spring 106. Once thigh link 102 reaches point $A_1$, another small torque pushes fourth link 108 at $B_1$ to be on trajectory 162. In the configuration described above, thigh link 102 moves from $A_1$ to $A_2$ and faces resistance from compression spring 106. However, from $A_2$ to $A_1$, thigh link 102 does not face any resistance from compression spring 106.

Figure 6:
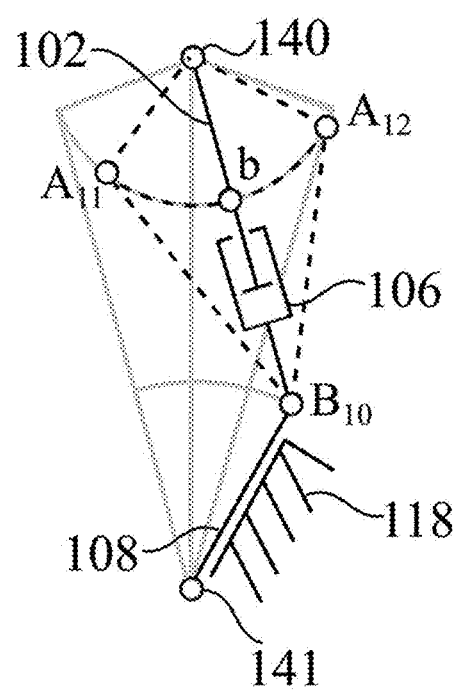
FIG. 6 depicts artificial knee 100 in a configuration that includes a toggle switch, configured in accordance with various embodiments.

FIG. 6 depicts artificial knee 100 in a configuration that includes a toggle switch, configured in accordance with various embodiments. Points $A_{11}$ and $A_{12}$ represent the locations of thigh link 102 when fourth link 108 (the follower link) is constrained. Both thigh link 102 and compression spring 106 (the coupler link) are shown by dashed lines in these boundary locations where fourth link 108 (the follower link) is constrained. As can be seen in FIG. 6, compression spring 106 starts to compress and resist the motion of thigh link 102 when thigh link 102 is at point $A_{11}$. This compression continues until joint A reaches point b where compression spring is at its shortest length. This means from $A_{11}$ to b, compression spring 106 provides extension torque for artificial knee 100. After point b, when thigh link 102 travels toward $A_{12}$, compression spring 106 switches its extension torque to flexion torque. This means the flexion motion of thigh link 102 from b to $A_{12}$ is encouraged by compression spring 106. As shown in FIG. 6, when fourth link 108 (follower link) is constrained, compression spring 106 (the coupler link) provides a compression force that passes through the coupling location of thigh link 102 relative to shank link 104 (associated with joint 140) when thigh link 102 is at point b (the toggle point). At point b, thigh link 102 and compression spring 106 are aligned, and compression spring 106 is at its shortest length. The toggle point, b, is an unstable equilibrium point for compression spring 106. When thigh link 102 moves from $A_{11}$ toward point b, compression spring 106 provides an extension torque between thigh link 102 and shank link 104. When thigh link 102 moves from b toward point $A_{12}$, compression spring 106 provides a flexion torque between thigh link 102 and shank link 104.

As described above, at singular points (point $B_1$ and $B_2$), small torques are utilized with reference to fourth link 108 to perturb fourth link 108 to move along trajectories 162 and 164 because thigh link 102 (the driver link) loses its ability to move four bar linkage 130. As will be discussed in greater detail below, these torques are provided by additional torque generators, such as first and second leaf springs 120 and 122.

Figure 7A:
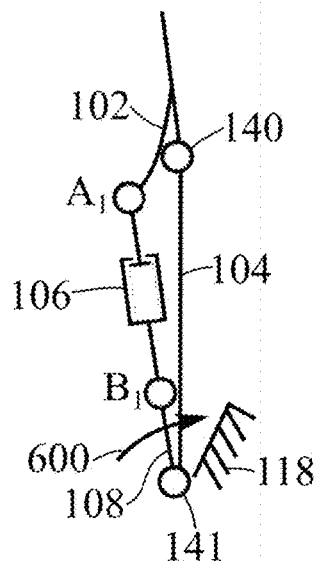
FIG. 7A, FIG. 7B, FIG. 7C, FIG. 7D, FIG. 7E, and FIG. 7F depicts how artificial knee 100 operates in a gait cycle, configured in accordance with various embodiments.

FIG. 7A, FIG. 7B, FIG. 7C, FIG. 7D, FIG. 7E, and FIG. 7F depict how artificial knee 100 operates in a gait cycle, configured in accordance with various embodiments. More specifically, FIG. 7A illustrates that artificial knee 100 is at a singular point where compression spring 106 (the coupler link) aligns with fourth link 108 (the follower link). Joint A is located at point $A_1$ and joint B is located at $B_1$. Knee angle $\theta_{KNEE}$ 700 at this instance is defined as start angle $\theta_{START}$ 800. With the application of a small torque along direction 600 on fourth link 108 (follower link), fourth link 108 (follower link) moves in a clockwise direction to break away from singular point, and transition the transmission angle μ to a negative value.

Figure 7B:
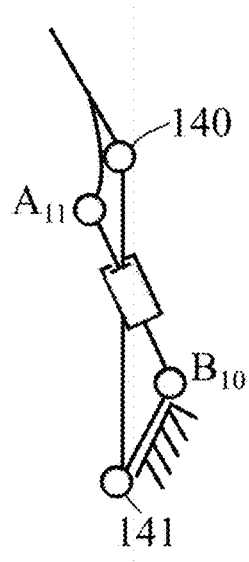

As thigh link 102 rotates in a counter-clockwise direction (as artificial knee 100 flexes), fourth link 108 (the follower link) rotates toward constraint 118 until fourth link 108 encounters constraint 118 as shown in FIG. 7B. Joint B is located at point $B_{10}$ and joint A is located at $A_{11}$. At this point, compression spring 106 begins to provide an extension torque as artificial knee 100 continues to flex. Moreover, at this point, knee angle $\theta_{KNEE}$ 700 is engagement angle $\theta_{ENG}$ 802, which is where the "extension support state" starts.

Figure 7C:
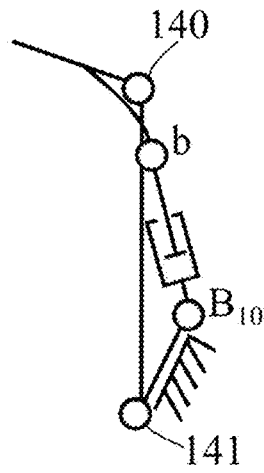

When thigh link 102 continues to rotate in a counter-clockwise direction, thigh link 102 reaches a point where thigh link 102 aligns with compression spring 106 (the coupler link) as shown in FIG. 7C. At this point, the extension torque generated by compression spring 106 (the coupler link) switches its direction and becomes a flexion torque. At this moment, the knee angle $\theta_{KNEE}$ 700 is the toggle angle $\theta_{TOG}$ 804 where the "flexion support state" starts. Joint A 300 is located at point b where the compression force of compression spring 106 passes through knee joint 140.

Figure 7D:
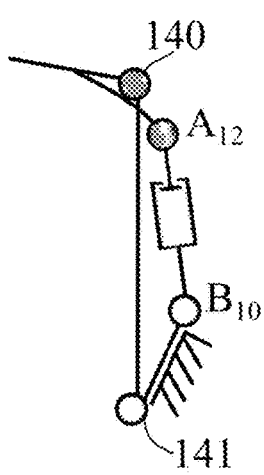

The flexion torque exists until compression spring 106 (the coupler link) reaches its original length as shown in FIG. 7D. Knee angle $\theta_{KNEE}$ 700, at this point, is the release angle $\theta_{REL}$ 806. Moreover, joint A is at point $A_{12}$.

Figure 7E:
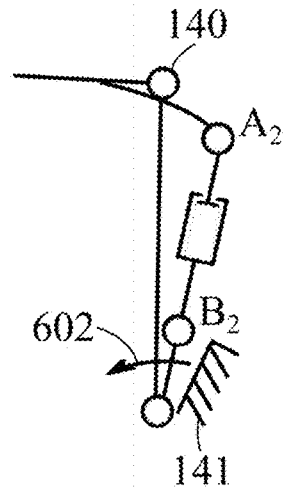

Thigh link 102 continues to rotate in a counter-clockwise direction until it reaches another singular point when knee angle $\theta_{KNEE}$ 700 is at end angle $\theta_{END}$ 808 as shown in FIG. 7E. At this point, joint A is at point $A_2$ and joint B is at point $B_2$. In some embodiments, a small torque on fourth link 108 (the follower link), along direction 602, causes fourth link 108 (the follower link) to rotate away from constraint 118. Transmission angle μ at this time switches from a negative to positive value.

Figure 7F:
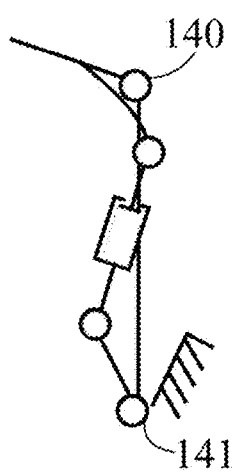

During knee extension as shown in FIG. 7F, thigh link 102 rotates in a clockwise direction, and fourth link 108 (the follower link) rotates away from constraint 118. In this example, thigh link 102 does not experience torque resistance when rotating in the clockwise direction. Thigh link 102 continues to rotate clockwise (during knee extension) and returns back to the configuration shown in FIG. 7A where artificial knee 100 is again at a singular point at which the transmission angle μ is on the verge of shifting signs.

The configuration of artificial knee 100 illustrated between FIG. 7E and FIG. 7A is considered a first free state because thigh link 102 encounters little to no resistance when it rotates in a clockwise direction. The configuration of artificial knee 100 between FIG. 7A and FIG. 7B is considered a second free state because thigh link 102 encounters little to no resistance when it rotates in a counter-clockwise direction. The configuration of artificial knee 100 between FIG. 7B and FIG. 7C is considered an extension support state because compression spring 106 provides extension torque between thigh link 102 and shank link 104. The configuration of artificial knee 100 between FIG. 7C and FIG. 7D is considered a flexion support state because compression spring 106 provides flexion torque between thigh link 102 and shank link 104. The configuration of artificial knee 100 between FIG. 7D and FIG. 7E is considered a third free state because thigh link 102 encounters little to no resistance when it rotates in a counter-clockwise direction.

Figure 8:
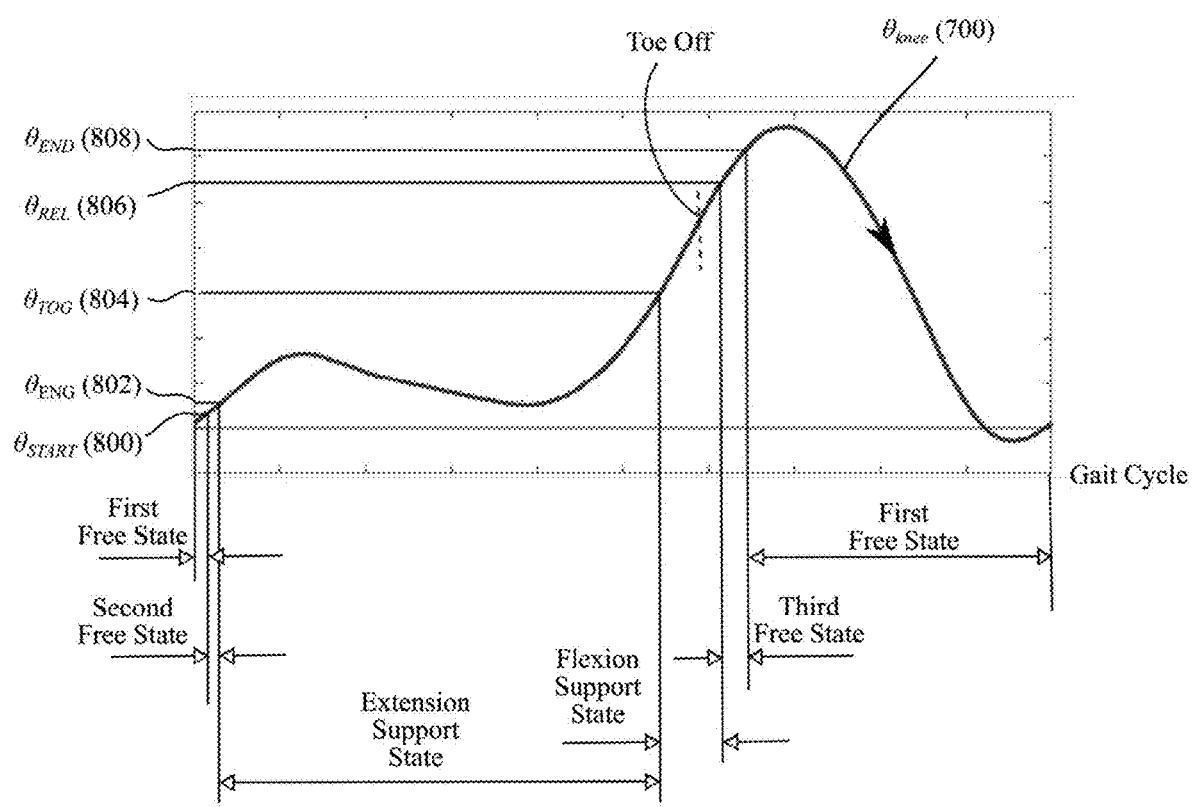
FIG. 8 depicts individual states of artificial knee 100 in a gait cycle as a function of knee angle $\theta_{KNEE}$ 700, implemented in accordance with various embodiments.

FIG. 8 depicts individual states of artificial knee 100 in a gait cycle as a function of knee angle $\theta_{KNEE}$ 700, implemented in accordance with various embodiments. Artificial knee 100 is in the first free state when it is flexing, and when knee angle $\theta_{KNEE}$ 700 is not larger than start angle $\theta_{START}$ 800. Artificial knee 100 is in the second free state when it is flexing, and when knee angle $\theta_{KNEE}$ 700 is between start angle $\theta_{START}$ 800 and engagement angle $\theta_{ENG}$ 802. Artificial knee 100 is in the extension support state when knee angle $\theta_{KNEE}$ 700 is between engagement angle $\theta_{ENG}$ 802 and toggle angle $\theta_{TOG}$ 804. Artificial knee 100 is in the flexion support state when it is flexing, and when knee angle $\theta_{KNEE}$ 700 is between toggle angle $\theta_{TOG}$ 804 and release angle $\theta_{REL}$ 806. Artificial knee 100 is in the third free state when knee angle $\theta_{KNEE}$ 700 is between release angle $\theta_{REL}$ 806 and end angle $\theta_{END}$ 808.

Figure 9:
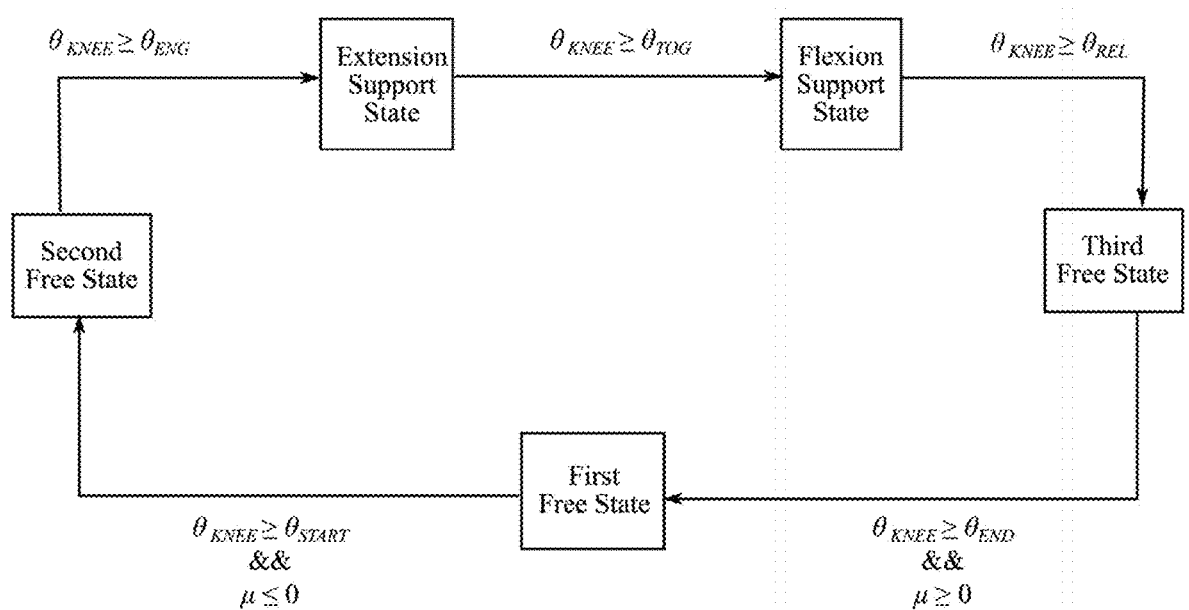
FIG. 9 depicts a finite state machine of artificial knee 100, configured in accordance with various embodiments.

FIG. 9 depicts a finite state machine of artificial knee 100, configured in accordance with various embodiments. As similarly discussed above, artificial knee 100 may progress through one or more states, such as a first free state, a second free state, an extension support state, a flection support state, and a third free state. As also discussed above, such states and transitions between states are determined based on a progression of knee angle $\theta_{KNEE}$ 700. In various embodiments, the solid lines show operation of artificial knee 100 as the knee angle $\theta_{KNEE}$ 700 progresses as shown in FIG. 8.

FIG. 10A, FIG. 10B, FIG. 10C, and FIG. 10D depict artificial knee 100 that includes extension link 112, configured in accordance with various embodiments. In various embodiments, extension link 112 allows knee angle $\theta_{KNEE}$ 700 to have a larger range of motion without impeding the operation of artificial knee 100, as shown above in FIG. 7. In various embodiments, artificial knee 100 has an extension link 112 that allows knee angle $\theta_{KNEE}$ 700 to expand larger than the knee angle at the singular configurations, such as start angle $\theta_{START}$ 800 as well as end angle $\theta_{END}$ 808. In one embodiment, extension link 112 can be an extension spring that is configured to lengthen the coupler, but is also configured to return the coupler to its shortest length. In various embodiments, extension link 112 is configured as a rigid link when it is not pulled so the aforementioned operation is not effected, but is further configured to become extendable when the knee reaches outside the boundary of singular configurations.

Figure 10A:
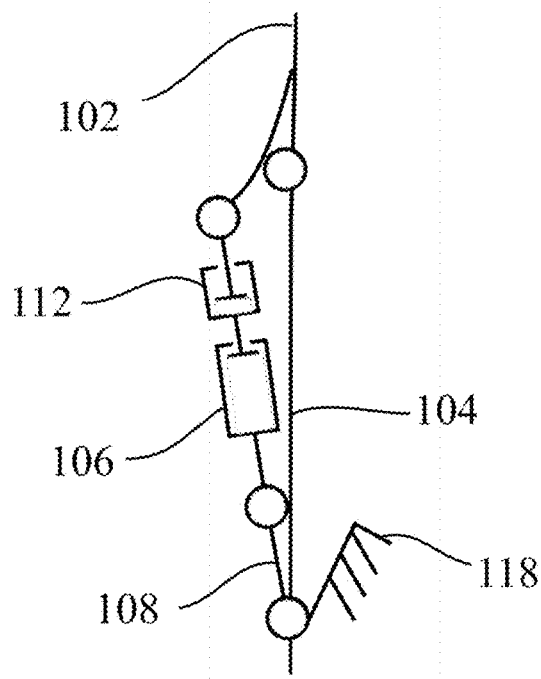
FIG. 10A, FIG. 10B, FIG. 10C, and FIG. 10D depict artificial knee 100 having extension link 112, configured in accordance with various embodiments.
Figure 10B:
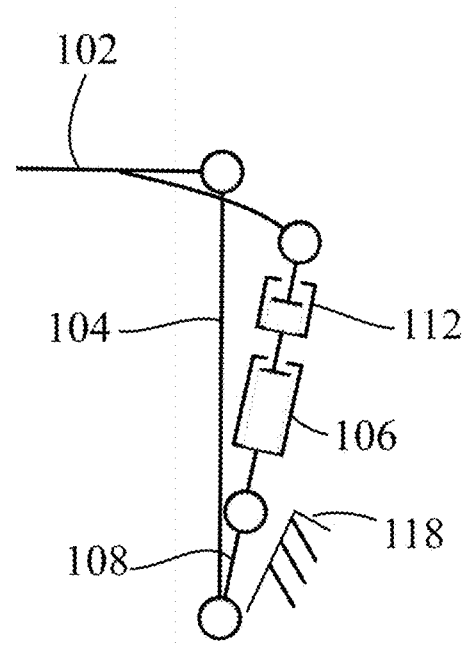

FIG. 10A and FIG. 10B illustrate various embodiments of artificial knee 100 and extension link 112, where a first end of extension link 112 is rotatably coupled to thigh link 102, and a second end of extension link 112 is linearly coupled to the first end 510 of compression spring 106. FIG. 10A depicts artificial knee 100 with extension link 112 configured to allow knee angle $\theta_{KNEE}$ 700 to be about 0 degrees. FIG. 10B depicts artificial knee 100 with extension link 112 configured to allow knee angle $\theta_{KNEE}$ 700 to be about 90 degrees.

Figure 10C:
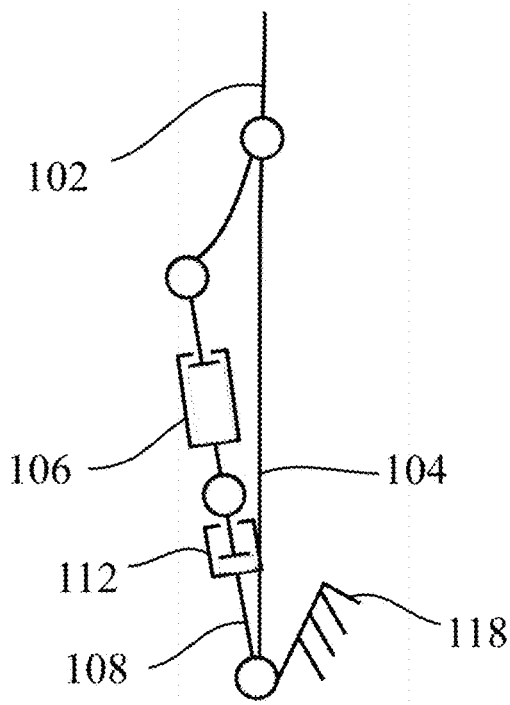
Figure 10D:
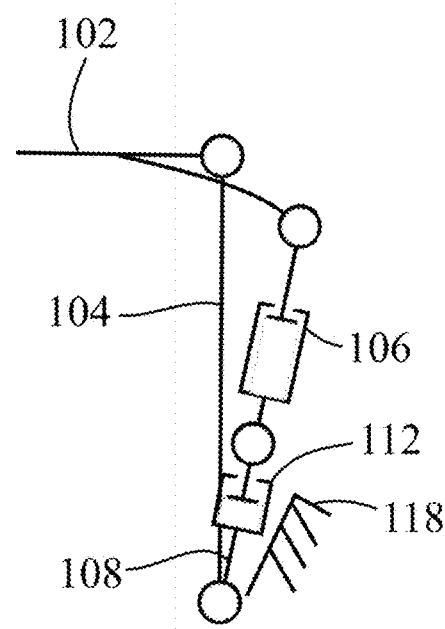

FIG. 10C and FIG. 10D show additional embodiments of artificial knee 100 with extension link 112, where the first end of extension link 112 is rotatably coupled to the second end 511 of compression spring 106, and the second end of extension link 112 is linearly coupled to fourth link 108 (the follower link). FIG. 10C depicts artificial knee 100 with extension link 112 configured to allow knee angle $\theta_{KNEE}$ 700 to be about 0 degrees. FIG. 10D depicts artificial knee 100 with extension link 112 configured to allow knee angle $\theta_{KNEE}$ 700 to be about 90 degrees.

Figure 11:
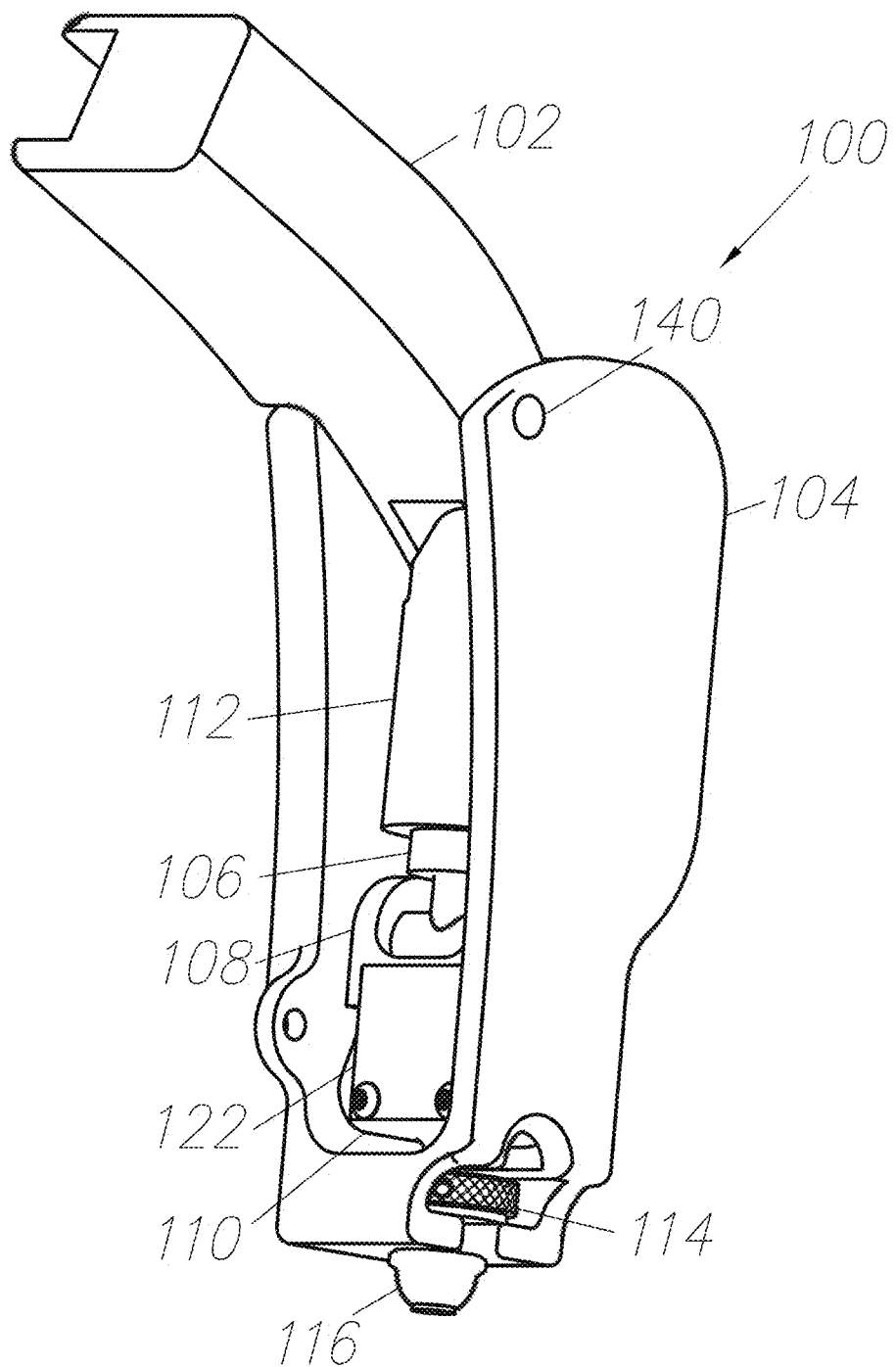
FIG. 11 depicts a mechanical configuration of artificial knee 100, configured in accordance with various embodiments.
Figure 12:
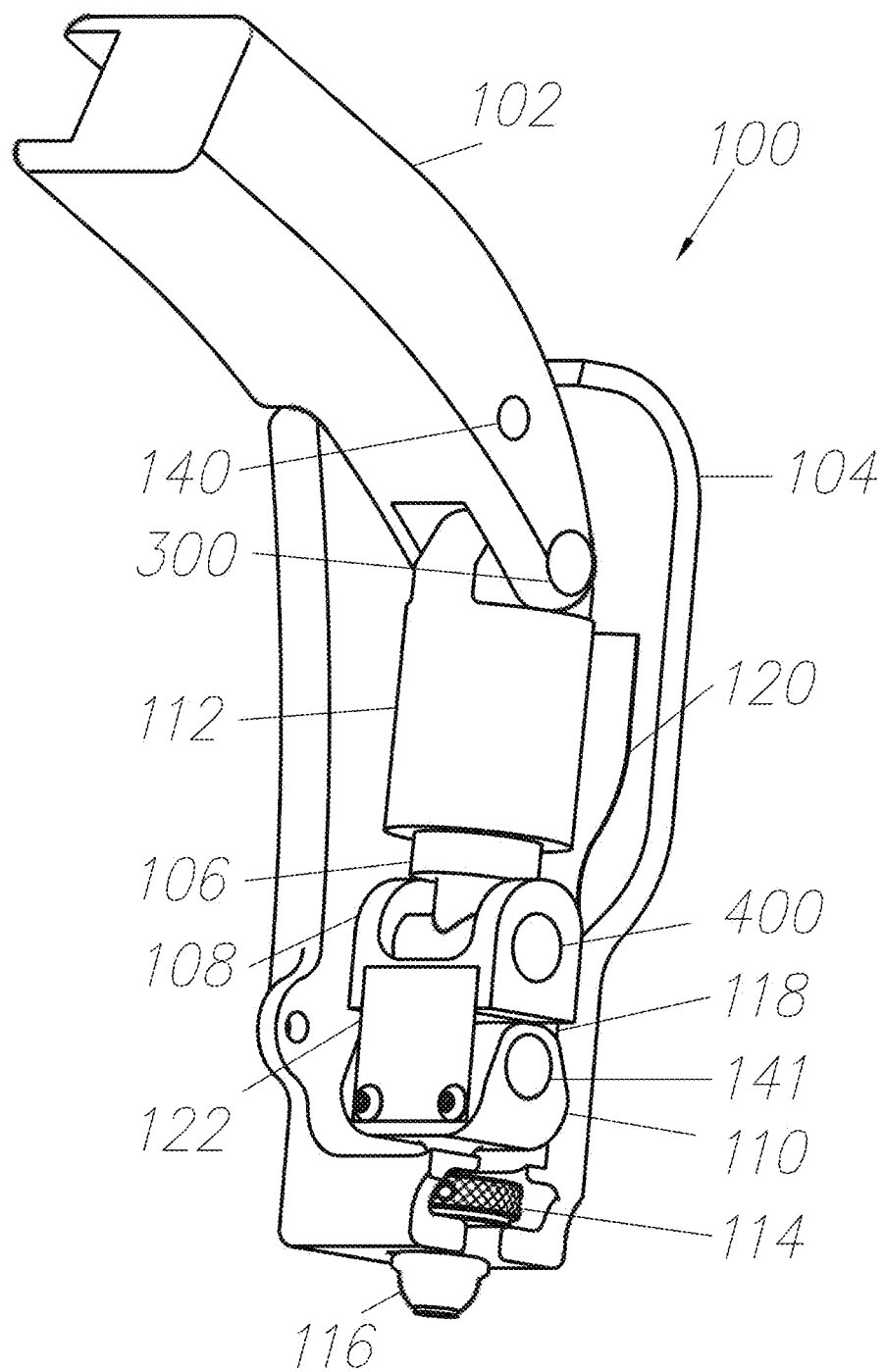
FIG. 12 depicts a cross-sectional view of the mechanical configuration of artificial knee 100, configured in accordance with various embodiments.
Figure 13:
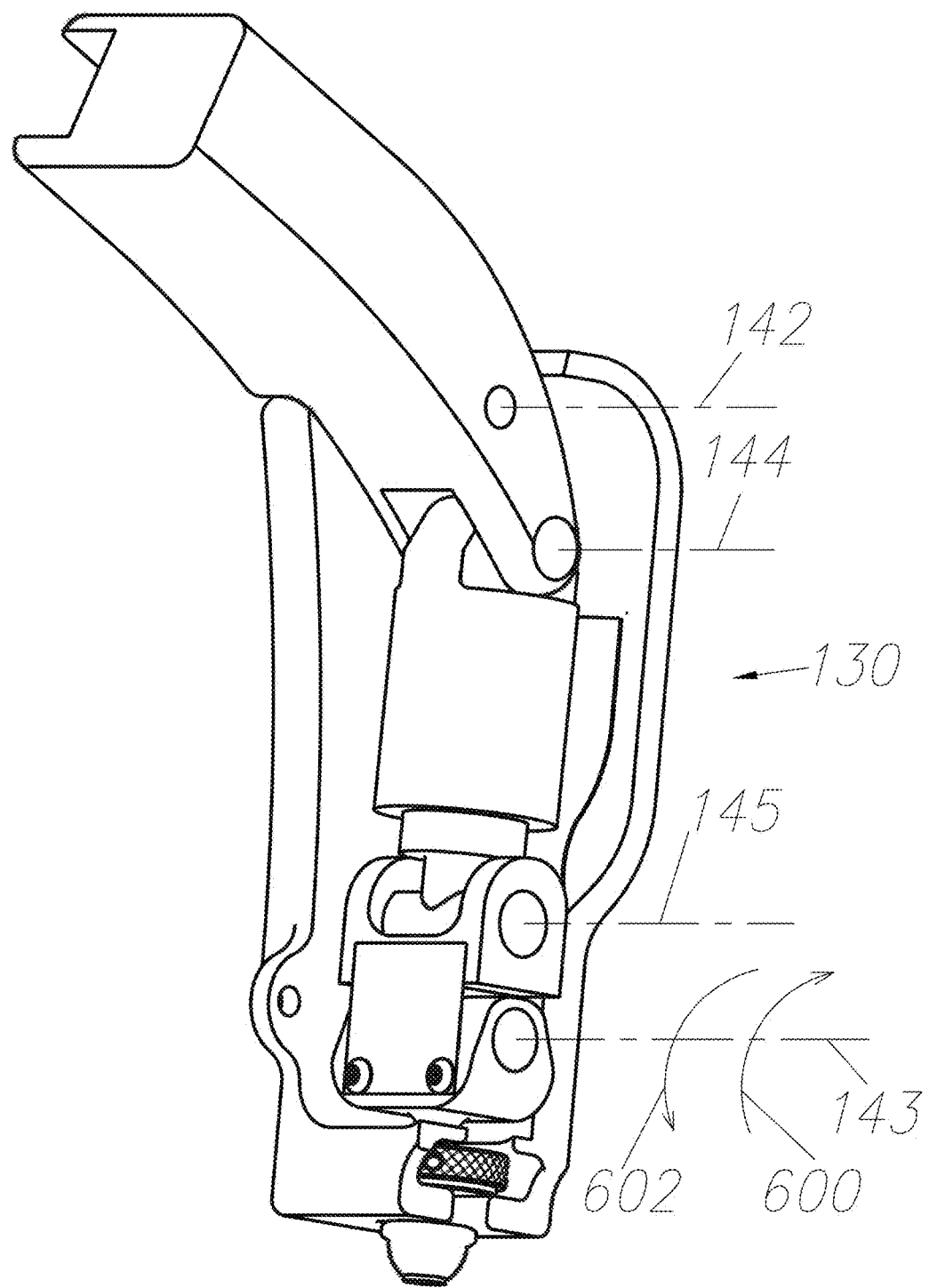
FIG. 13 depicts another cross-sectional view of the mechanical configuration of artificial knee 100, but further illustrating an indication of the rotating axes of four bar linkage 130, configured in accordance with various embodiments.

FIG. 11 depicts a mechanical configuration of artificial knee 100, configured in accordance with various embodiments. FIG. 12 depicts a cross-sectional view of the mechanical configuration of artificial knee 100 as shown in FIG. 11, configured in accordance with various embodiments. FIG. 13 depicts another cross-sectional view of the mechanical configuration of artificial knee 100 as shown in FIG. 12, but further illustrating an indication of the rotating axes of four bar linkage 130, configured in accordance with various embodiments. In this example, extension link 112 is rotatably coupled with thigh link 102, and linearly coupled with compression spring 106. Accordingly, as discussed above, and illustrated in at least FIG. 11, FIG. 12 and FIG. 13, artificial knee 100 includes thigh link 102 that is configured to move in unison with the person's thigh. Artificial knee 100 further includes shank link 104 which is configured to move in unison with the person's shank and is rotatably coupled to thigh link 102. Thigh link 102 and shank link 104 rotate relative to each other about knee joint 140. Axis 142 represents the axis of knee joint 140 (rotation of thigh link 102 relative to shank link 104). Artificial knee 100 further comprises a compression spring 106 which is rotatably coupled to thigh link 102 at joint A 300. Axis 144 represents the rotation axis of joint A 300 (rotation of compression spring 106 relative thigh link 102). Compression spring 106 is rotatably coupled with fourth link 108 (the follower link) from its second end 512 at Joint B 400. Axis 145 represents the rotational axis of joint B 400 (rotation of fourth link 108 relative compression spring 106). Fourth link 108 is rotatably coupled to shank link 104 at Joint C 141. Axis 143 represents the rotational axis of joint C 141 (rotation of fourth link 108 relative to shank link 104).

Figure 14:
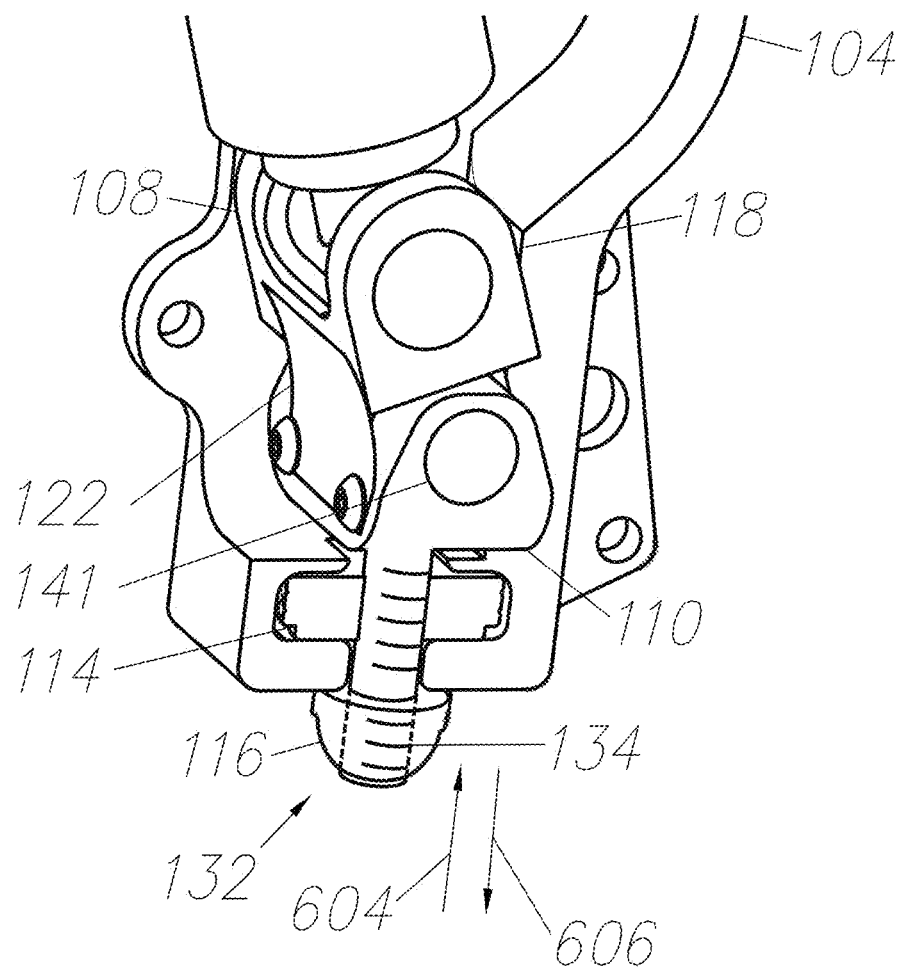
FIG. 14 depicts an example of adjustment mechanism 132 which may be implemented with configurations of artificial knee 100, configured in accordance with various embodiments.

FIG. 14 depicts an example of adjustment mechanism 132 which may be implemented with the above described configurations of artificial knee 100, configured in accordance with various embodiments. As will be discussed in greater detail below, adjustment mechanism 132 includes adjuster 110 rotatably coupled to fourth link 108 at a first end, and slidably coupled to shank link 104 at a second end. Moreover, adjustment mechanism 132 is configured to change the length between knee joint 140 and joint C 141. In this way, adjustment mechanism 132 is configured to allow a user to change or adjust the length of shank link 104 (the ground link).

Figure 15:
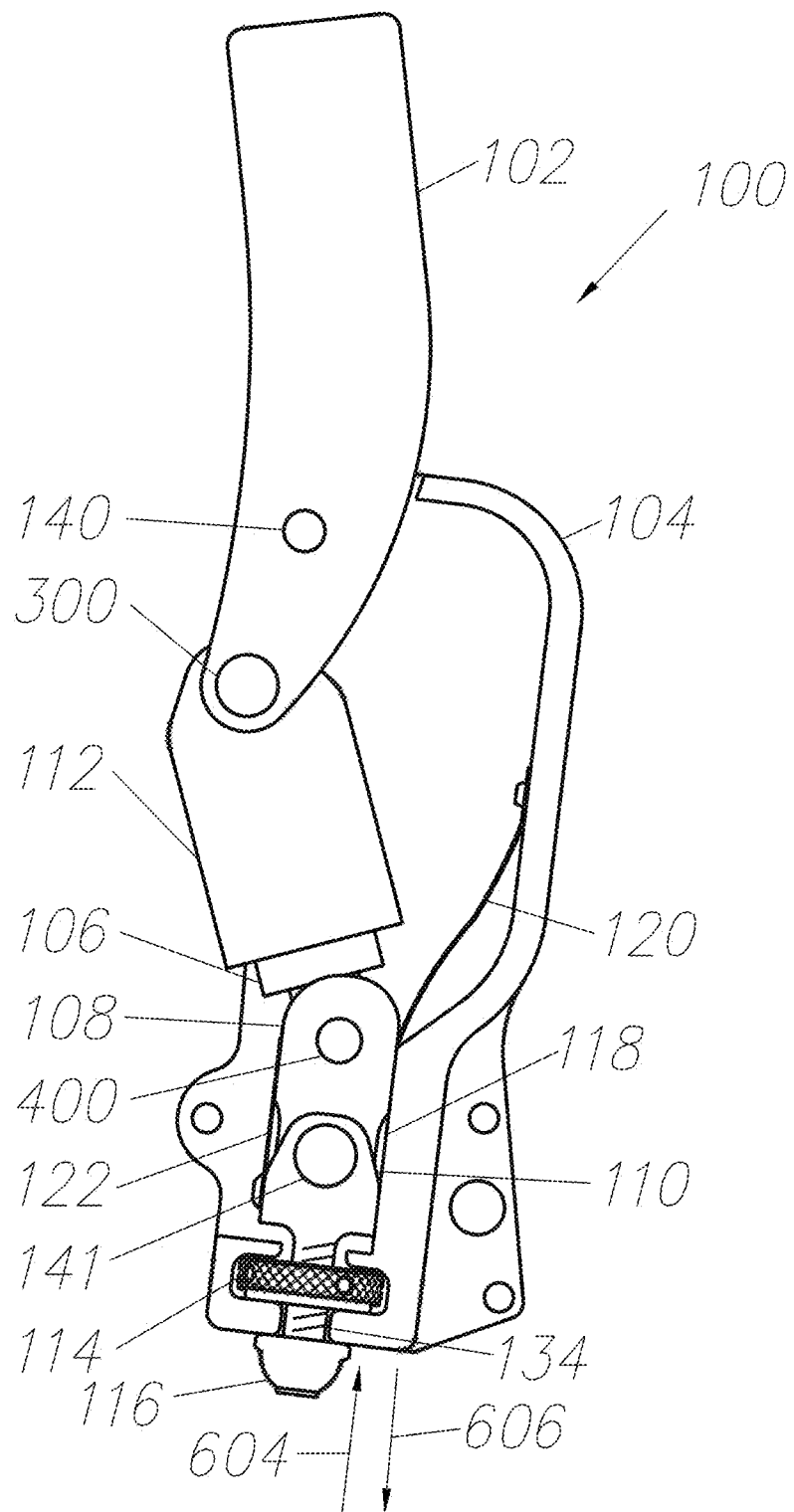
FIG. 15 and FIG. 16 illustrate adjustment mechanism 132 affecting engagement angle 802, configured in accordance with various embodiments.
Figure 16:
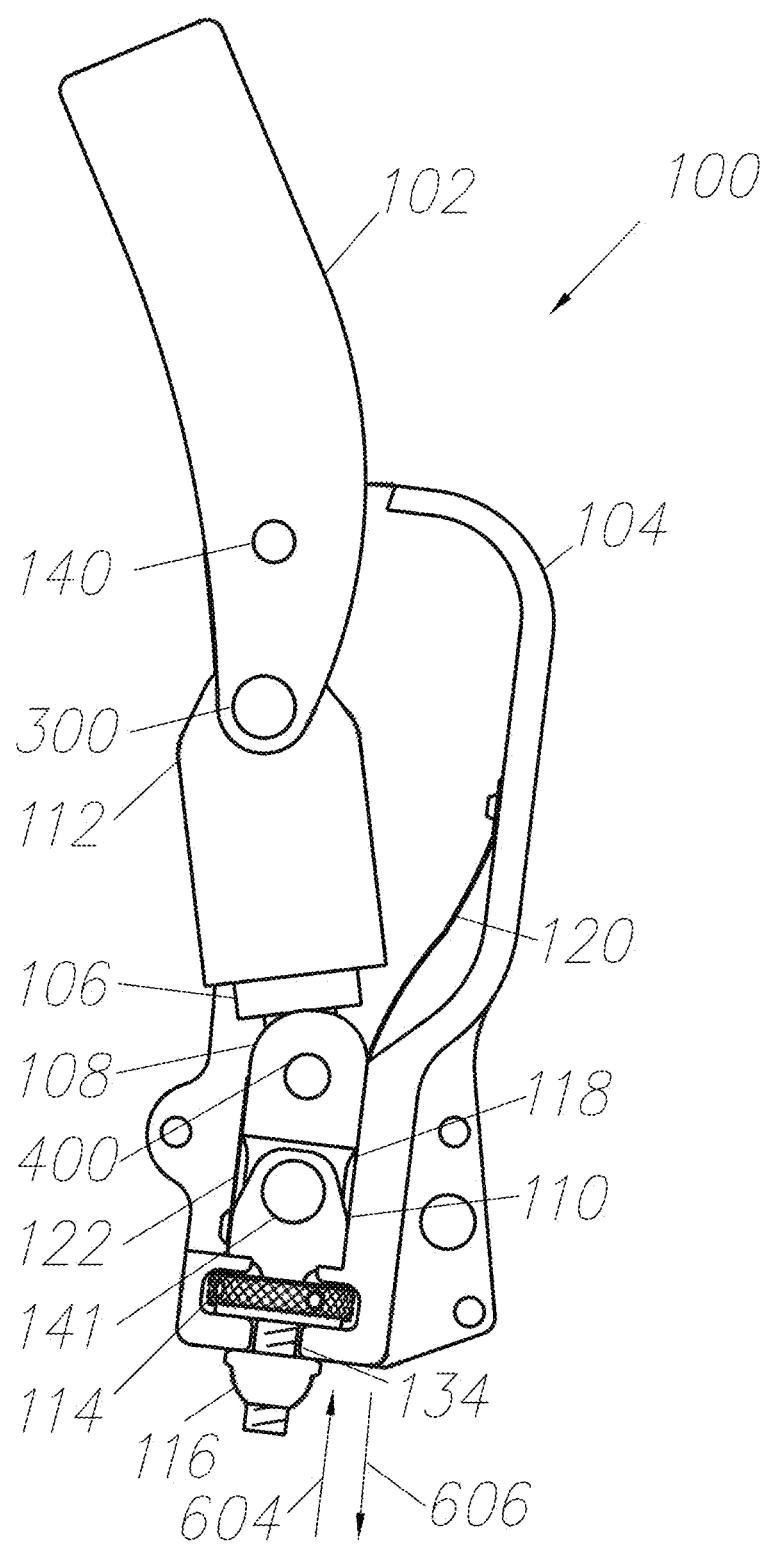

FIG. 15 and FIG. 16 illustrate adjustment mechanism 132 affecting engagement angle $\theta_{ENG}$ 802, configured in accordance with various embodiments. More specifically, FIG. 15 depicts artificial knee 100 further including first leaf spring 120. FIG. 16 shows adjuster 110 moved in direction 606, as compared to FIG. 15, while knee angle $\theta_{KNEE}$ 700 is at engagement angle $\theta_{ENG}$ 802. In various embodiments, a first end of first leaf spring 120 is coupled to shank link 104, and a second end of first leaf spring 120 is configured to apply torque in direction 602 on fourth link 108 (the follower link). First leaf spring 120 is configured to cause fourth link 108 (follower link) to move along trajectory 164 as shown in FIG. 5B. Artificial knee 100 further includes second leaf spring 122. A first end of second leaf spring 122 is coupled to shank link 104, and a second end of second leaf spring 122 is configured to apply torque in direction 600 on fourth link 108 (follower link). Second leaf spring 122 is configured to cause fourth link 108 (follower link) to move along trajectory 162 as shown in FIG. 5A. In some embodiments, first leaf spring 120 and second leaf spring 122 can be combined into one single spring, or other type of torque generators, such as magnets. In this way, first leaf spring 120 and second leaf spring 122 are configure to generate torques causing fourth link 108 (follower link) to move along trajectories 164 and 166.

As discussed above, artificial knee 100 may further include constraint 118, which may be coupled to shank link 104. In some embodiments, constraint 118 is a feature of shank link 104. Constraint 118 is configured to block the motion of fourth link 108 when fourth link 108 moves along trajectory 162 shown in FIG. 5A.

In some embodiments, as shown in FIG. 14, FIG. 15, and FIG. 16, artificial knee 100 further includes adjustment mechanism 132 that is configured to change the length between knee joint 140 and joint C 141. In this way, adjustment mechanism 132 is configured to allow a user to change the length of shank link 104 (the ground link) shown in FIG. 3. Additional details are provided below regarding how adjustment mechanism 132 provides various functionalities for artificial knee 100. In various embodiments, adjustment mechanism 132 includes adjuster 110 rotatably coupled to fourth link 108 at a first end, and slidably coupled to shank link 104 at a second end. In various embodiments, external threads of adjuster 110 pass through a hole in shank link 104. Adjustment mechanism 132 further includes thumb nut 114 and lock nut 116. By turning both thumb nut 114 and lock nut 116, adjuster 110 moves along direction 604 and 606 relative to shank link 104. In this way, the location of rotary joint C 141 with respect to knee joint 140 can be adjusted. The combination of thumb nut 114 and lock nut 116 secure adjuster 110 to shank link 104. Various other adjustment mechanisms may be utilized and configured to change the length of shank link 104 (the ground link). FIG. 16 further illustrates when adjuster 110 has moved along direction 606 in comparison with the configuration shown in FIG. 15. The engagement angle $\theta_{ENG}$ 802 in the configuration shown by FIG. 16 is larger than the engagement angle $\theta_{ENG}$ 802 in the configuration shown by FIG. 15.

Figure 17:
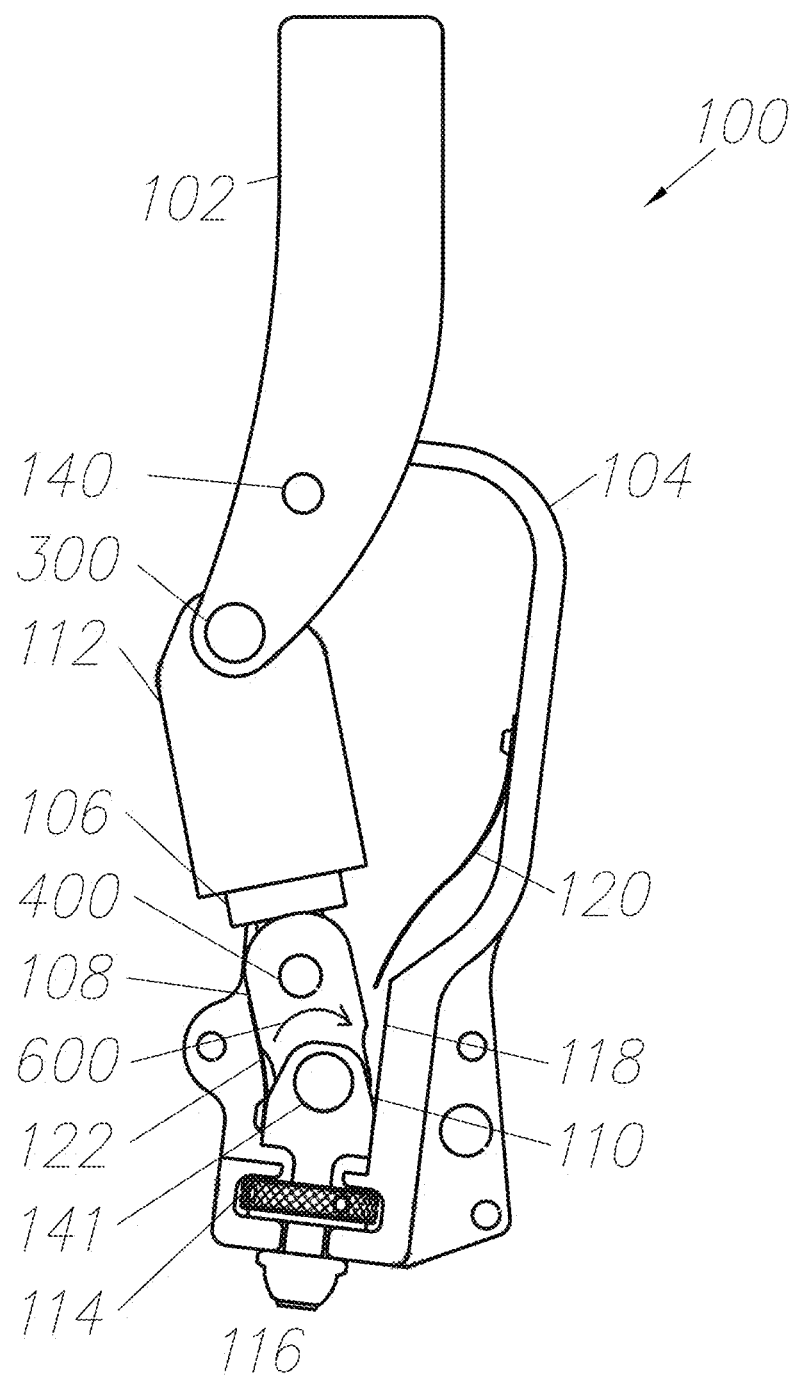
FIG. 17, FIG. 18, FIG. 19, FIG. 20, FIG. 21, and FIG. 22 depict a cross-sectional view of a mechanical configuration of artificial knee 100 operating in a gait cycle, implemented in accordance with various embodiments.

FIG. 17, FIG. 18, FIG. 19, FIG. 20, FIG. 21, and FIG. 22 depict cross-sectional views of a configuration of artificial knee 100 operating in a gait cycle, implemented in accordance with various embodiments. FIG. 17 represents artificial knee 100, as previously discussed with reference to at least FIG. 7A. FIG. 17 represents a configuration when knee angle $\theta_{KNEE}$ 700 is equal to start angle $\theta_{START}$ 800. In this configuration, compression spring 106 (the coupler link) aligns with fourth link 108 (the follower link). This configuration is schematically shown by FIG. 7A. Second leaf spring 122 pushes fourth link 108 (the follower link) with a torque along direction 600. When in this configuration, artificial knee 100 is at the border of the first free state and the second free state.

Figure 18:
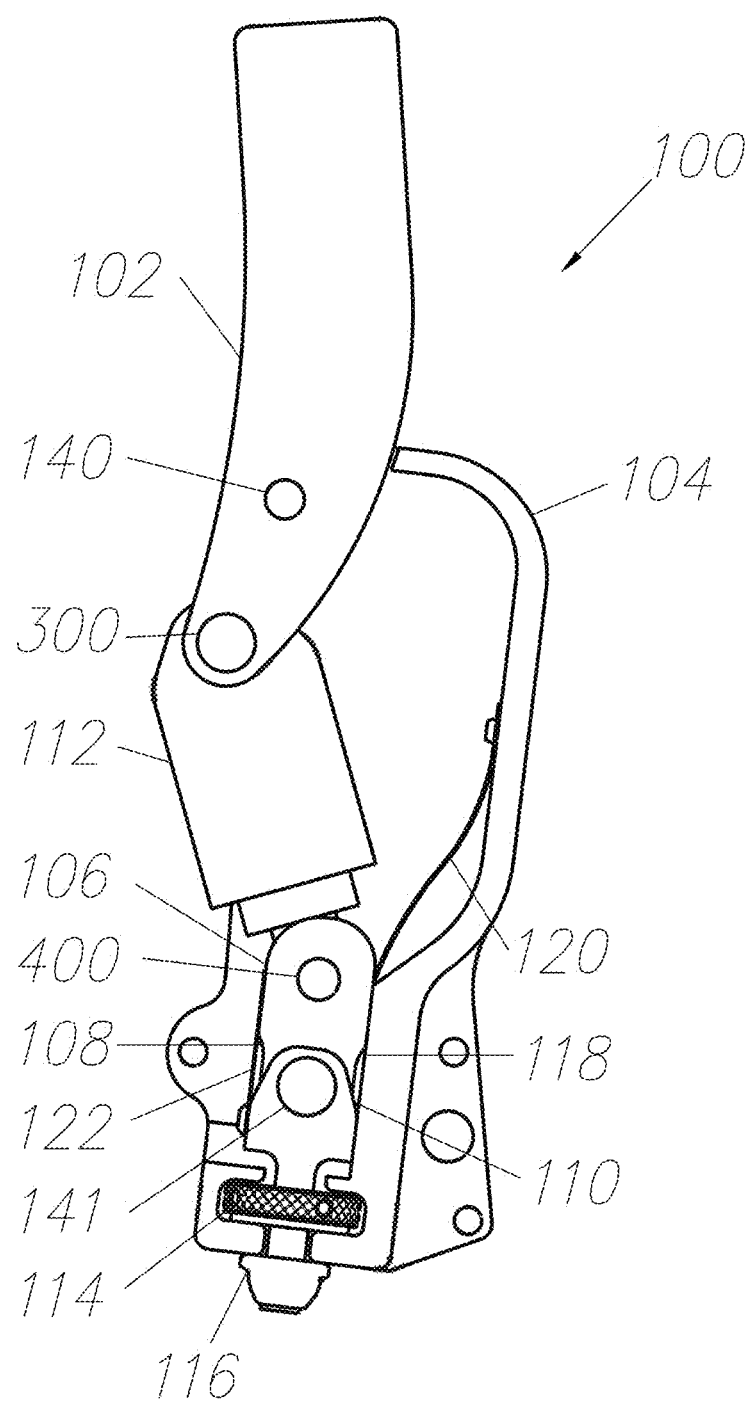
Figure 19:
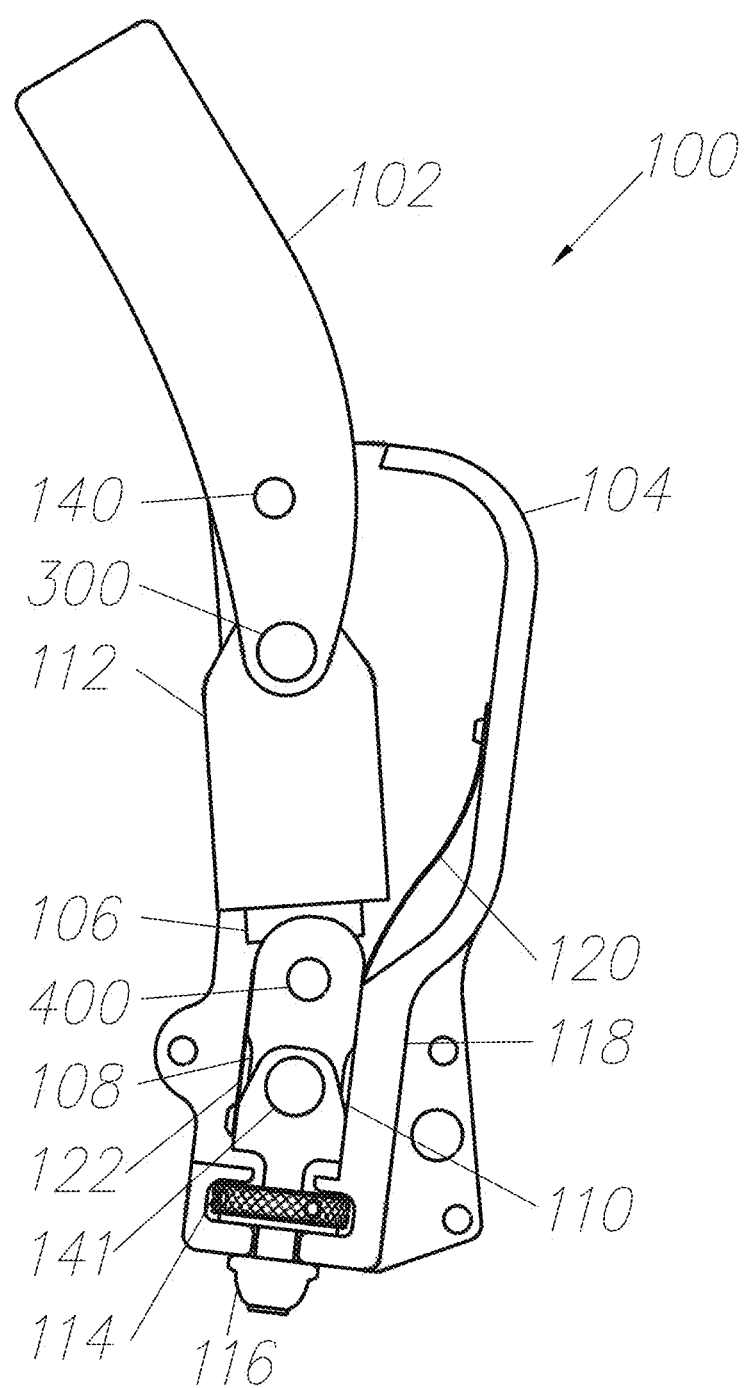
Figure 20:
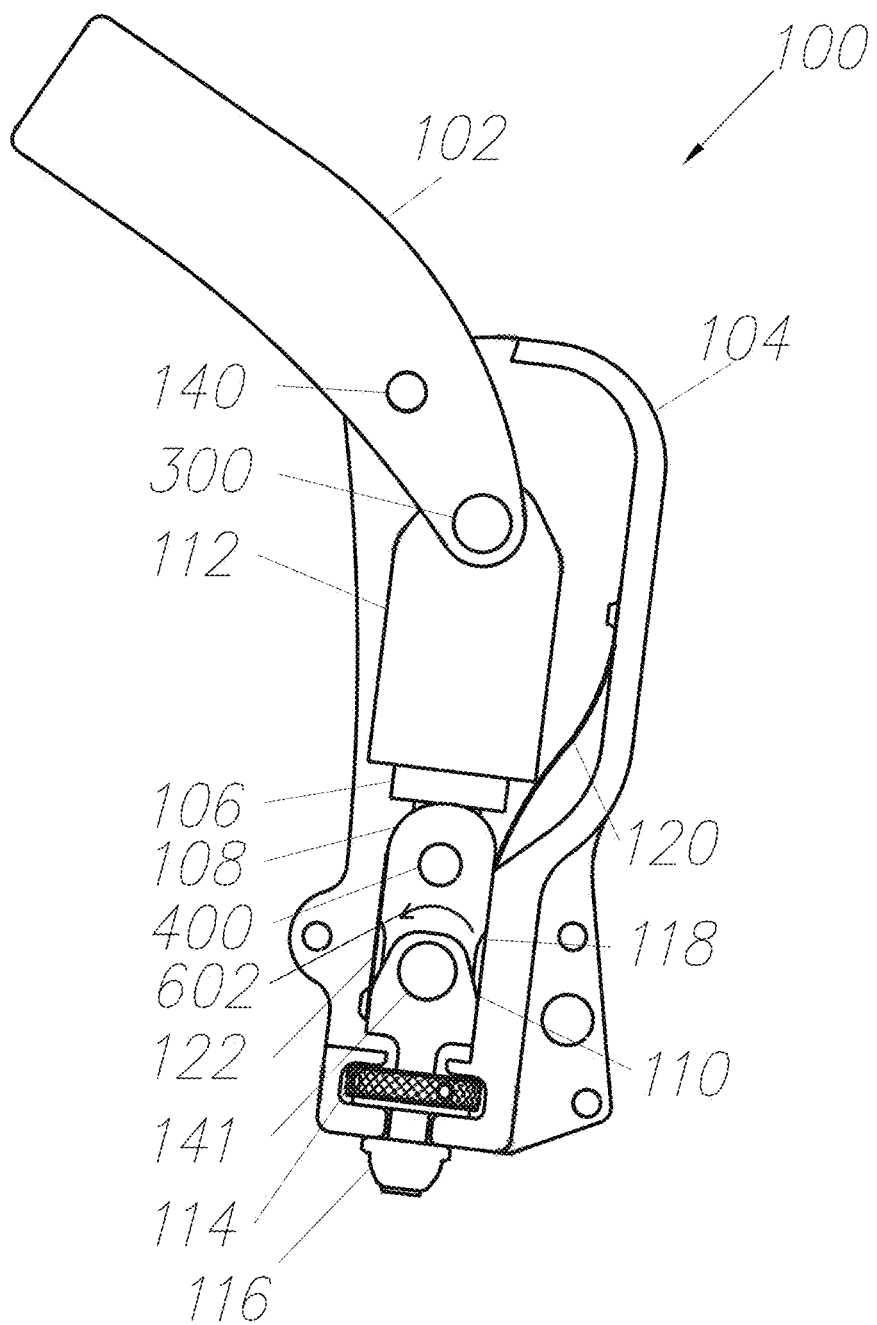

FIG. 18 depicts artificial knee 100 when fourth link 108 is constrained (blocked) by constraint 118 and the compressive spring 106 is about to be compressed. Knee angle $\theta_{KNEE}$ 700 in FIG. 18 is equal to engagement angle $\theta_{ENG}$ 802. Artificial knee 100, when in this configuration, is at the border of the second free state and the extension support state. This configuration is schematically shown by FIG. 7B. After this instance, as knee angle $\theta_{KNEE}$ 700 increases, compressive spring 106 gets compressed (gets shorter) and provides extension torque about knee joint 140. FIG. 19 depicts artificial knee 100 when knee angle $\theta_{KNEE}$ 700 is equal to toggle angle $\theta_{TOG}$ 804. Fourth link 108 is constrained by constraint 118 and compressive spring 106 aligns with knee joint 140. The torque from compressive spring 106 is zero when in this configuration and compressive spring 106 is at its maximum compression force. Artificial knee 100, when in this configuration, is at the border of the extension support state and the flexion support state. This is schematically shown in FIG. 7C. As knee angle $\theta_{KNEE}$ 700 increases, compressive spring 106 starts to provide flexion torque about knee joint 140 to encourage knee flexion. FIG. 20 depicts artificial knee 100 when knee angle $\theta_{KNEE}$ 700 is equal to release angle $\theta_{REL}$ 806. Fourth link 108, when in this configuration, is free to move away from constraint 118. Compressive spring 106, when in this configuration, completes generating compressive force and it returns to its original length. Artificial knee 100, when in this configuration, is at the border of the flexion support state and third free state. This is schematically shown in FIG. 7D. As knee angle $\theta_{KNEE}$ 700 increases in this configuration, compressive spring 106 does not provide torque on knee joint 140.

Figure 21:
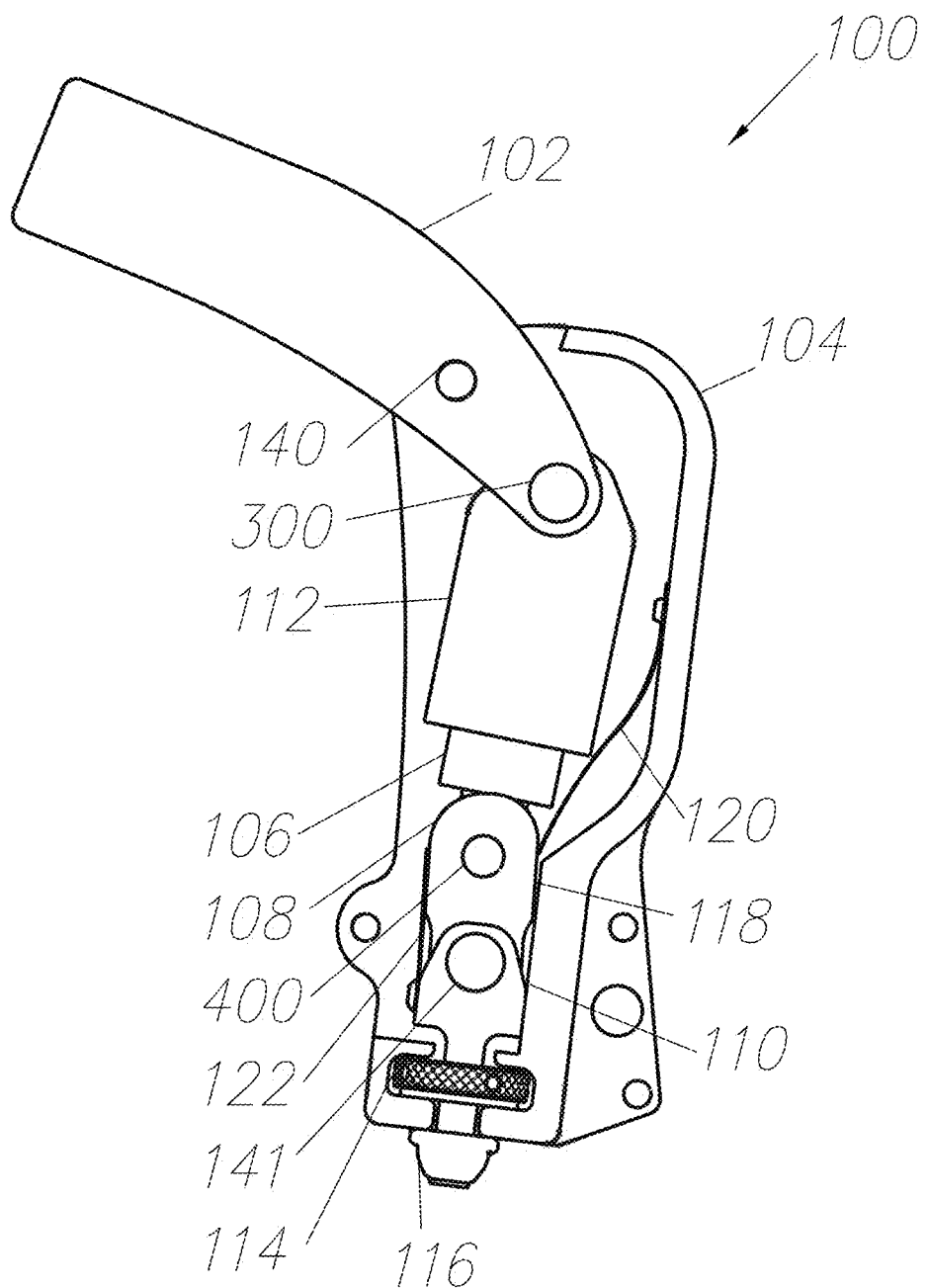
Figure 22:
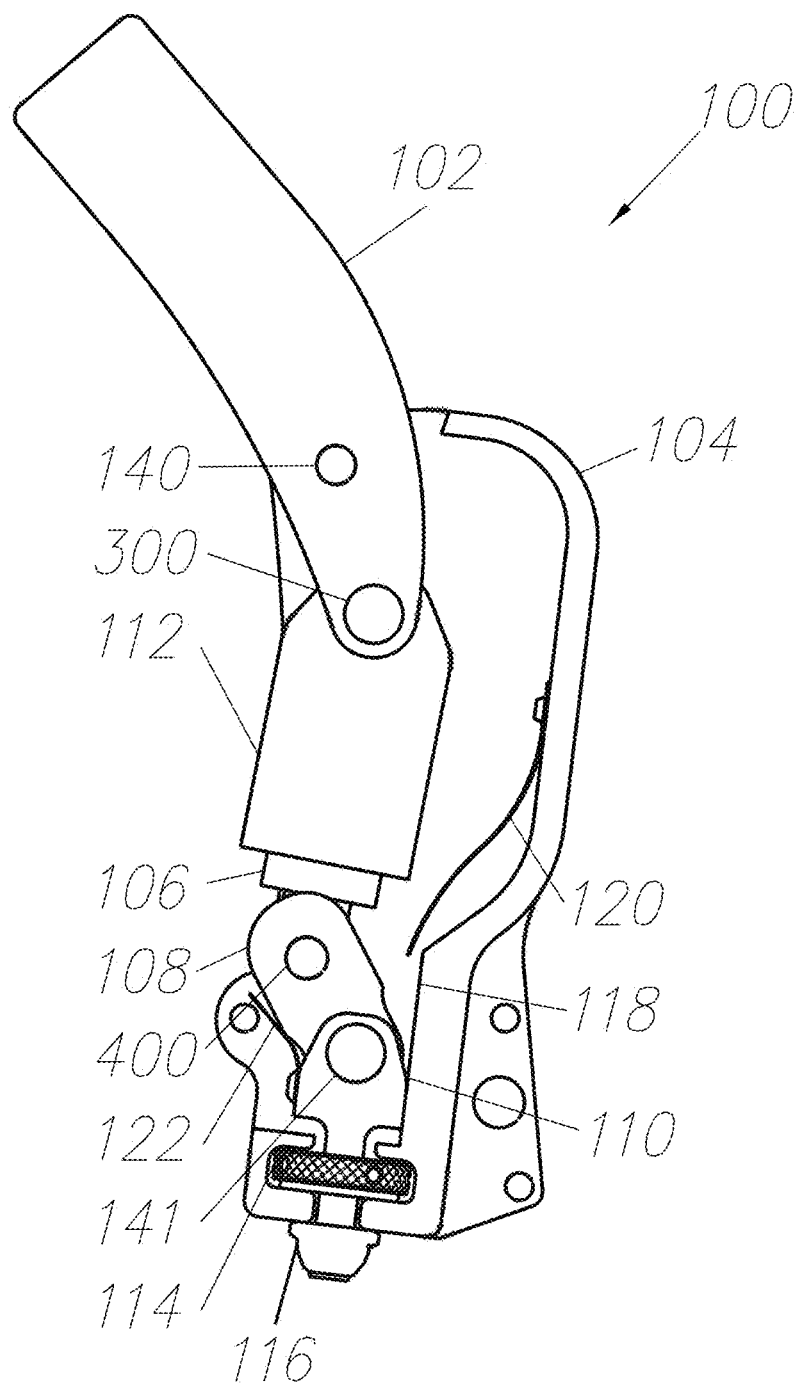
Figure 23:
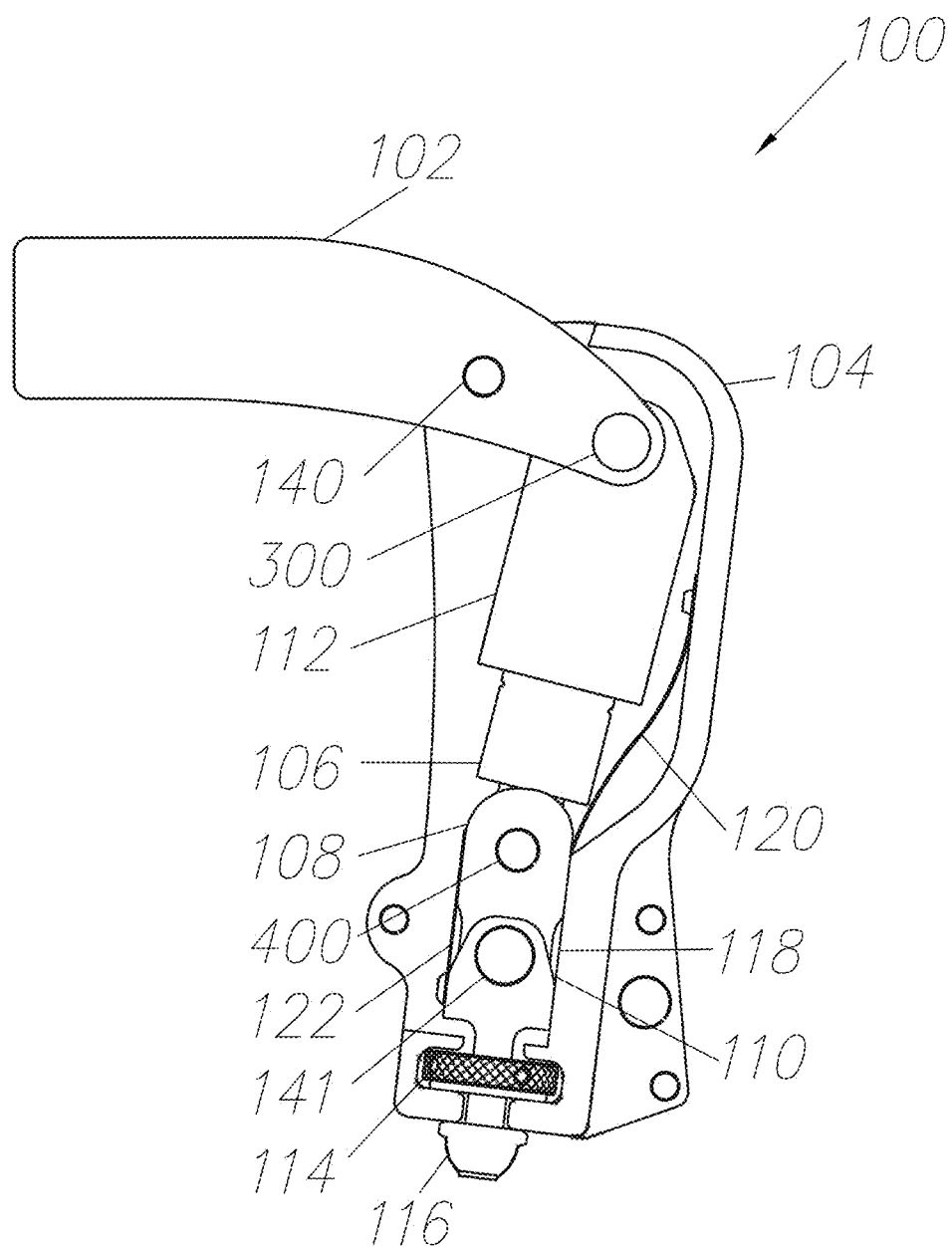
FIG. 23 depicts a cross-sectional view of the mechanical configuration of artificial knee 100 shown in FIG. 11 where the knee angle $\theta_{KNEE}$ 700 is 90 degrees, configured in accordance with various embodiments.

In various embodiments, end angle $\theta_{END}$ 808 is close to release angle $\theta_{REL}$ 806. Therefore, the knee $\theta_{KNEE}$ 700 is at release angle $\theta_{REL}$ 806, which are about the same as end angle $\theta_{END}$ 808, as shown in FIG. 20. Moreover, compression spring 106 (the coupler link) also aligns with fourth link 108 (follower link), and first leaf spring 120 pushes the fourth link 108 (follower link) to direction 602. When in this configuration, artificial knee 100 is at the border of the third free state and the first free state. This is schematically shown in FIG. 7E. FIG. 21 depicts artificial knee 100 when knee angle $\theta_{KNEE}$ 700 is larger than end angle $\theta_{END}$ 808. The extension of extension link 112 allows knee angle $\theta_{KNEE}$ 700 to be able to go beyond end angle $\theta_{END}$ 808. Artificial knee 100 is in the first free state. As knee angle $\theta_{KNEE}$ 700 returns back to end angle $\theta_{END}$ 808, first leaf spring 120 pushes fourth link 108 (follower link) in direction 602. FIG. 22 depicts artificial knee 100 when knee angle $\theta_{KNEE}$ 700 returns back to start angle $\theta_{START}$ 800 while artificial knee 100 is in the first free state. FIG. 23 depicts a cross-sectional view of the mechanical configuration of artificial knee 100 shown in FIG. 11 where the knee angle $\theta_{KNEE}$ 700 is 90 degrees, configured in accordance with various embodiments. When in this configuration, artificial knee 100 is in the first free state 900.

Figure 24:
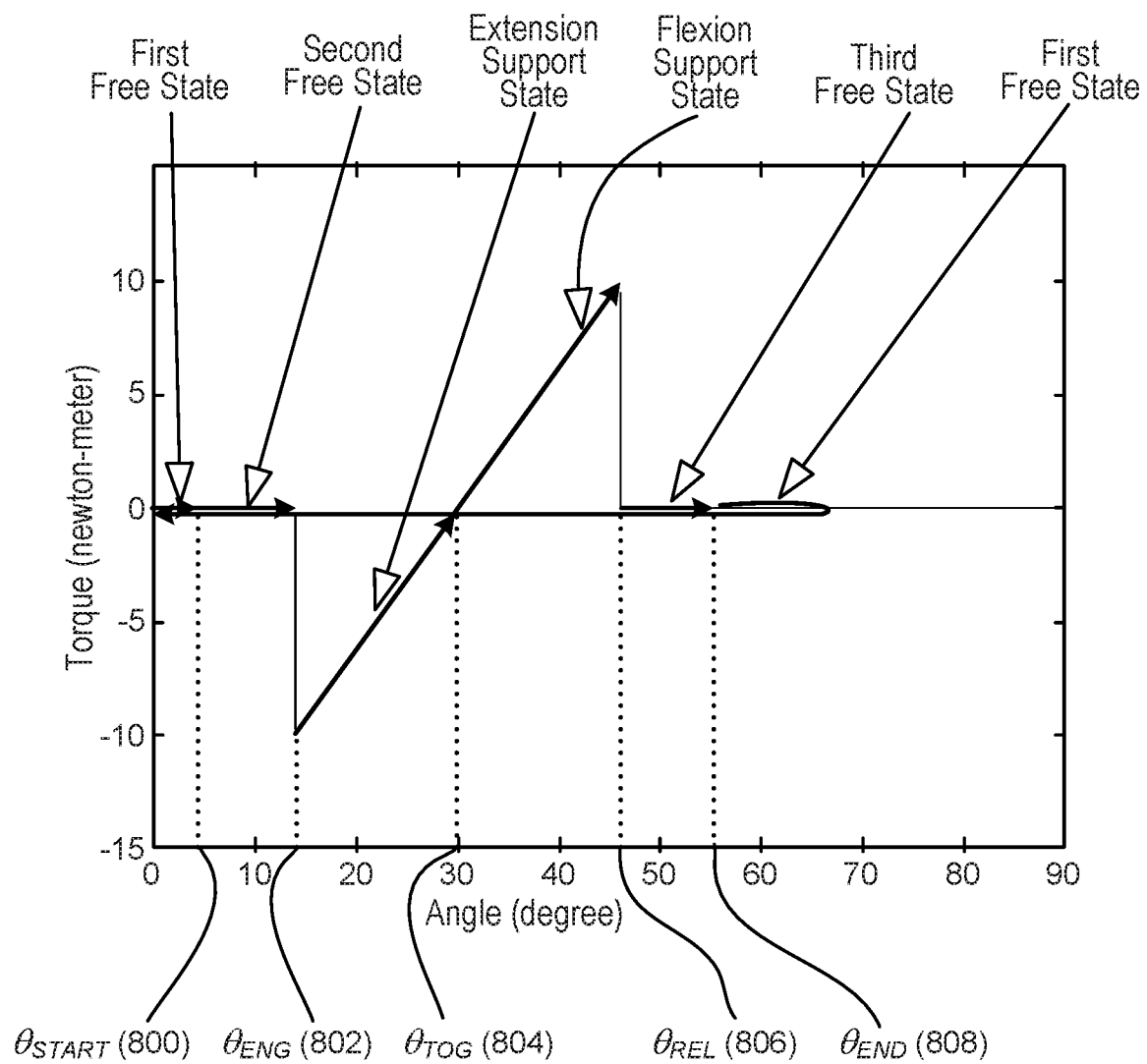
FIG. 24 depicts an example of a torque profile of artificial knee 100, implemented in accordance with various embodiments.

FIG. 24 depicts an example of a torque profile of artificial knee 100, implemented in accordance with various embodiments. In the first free state, the second free state, and the third free state, artificial knee 100 provides no torque. In extension support state, artificial knee 100 provides extension torque that facilitates a decrease of knee angle $\theta_{KNEE}$ 700. In flexion support state, artificial knee 100 provides flexion torque that facilitates an increase of knee angle $\theta_{KNEE}$ 700.

Figure 25A:
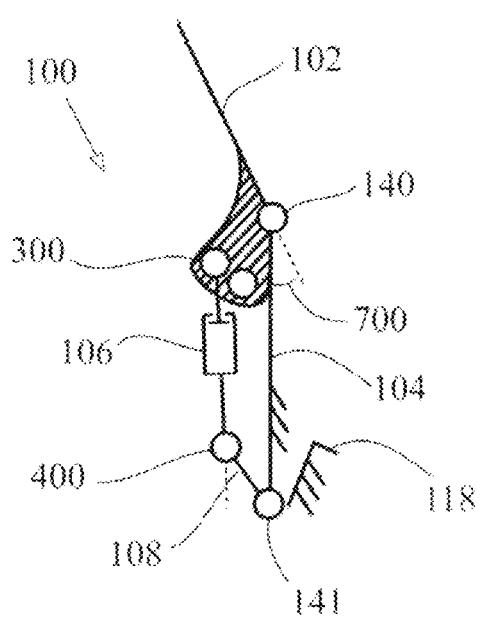
FIG. 25A and FIG. 25B depict an artificial knee 100 where toggle angle $\theta_{TOG}$ 804 is adjustable, configured in accordance with various embodiments.
Figure 25B:
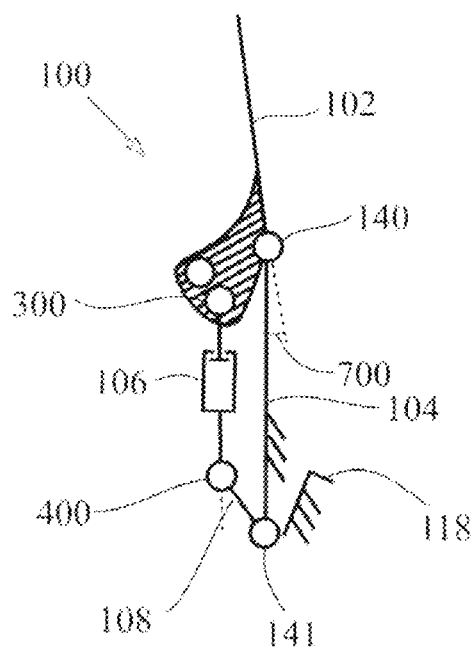

In various embodiments, toggle angle $\theta_{TOG}$ 804 is adjustable. Accordingly, FIG. 25A and FIG. 25B depict an artificial knee 100 where toggle angle $\theta_{TOG}$ 804 is adjustable, configured in accordance with various embodiments. In various embodiments, different locations of a rotating point of first end 510 of compressive spring 106 on thigh link 102 provide one or more different positions configured to switch toggle angle $\theta_{TOG}$ 804. Various adjustment mechanisms may be implemented to change toggle angle $\theta_{TOG}$ 804.

FIG. 26 depicts an embodiment of artificial knee 100 worn by person 200 as an orthotics knee, configured in accordance with various embodiments. FIG. 26 additionally illustrates artificial knee 100 coupled with ankle-foot orthotics 210. In some embodiments, ankle-foot orthosis 210 is configured to be coupled to a person's foot. In various embodiments, ankle-foot orthosis 210 is configured to be connected with shank link 104. Ankle-foot orthotics 210 maybe any suitable internal or external ankle-foot-orthoses. In some embodiments, artificial knee 100 is coupled to person 200 through thigh brace 206 and shank brace 208. Although embodiments disclosed herein describe braces used to couple shank link 104 and thigh link 102 to a person's thigh 202 and a person's shank 204, any suitable device or technique may be used for such coupling that would enable thigh link 102 and shank link 104 to move in unison with person's thigh 202 and person's shank 204.

FIG. 27 depicts an embodiment of artificial knee 100 worn by person 200 as an exoskeleton knee, configured in accordance with various embodiments. FIG. 27 shows artificial knee 100 further coupled to exoskeleton 211 by coupling thigh link 102 to exoskeleton thigh 212, and shank link 104 to exoskeleton shank 214. In some embodiments, exoskeleton thigh 212 and exoskeleton shank 214 move in unison with person's thigh 202 and person's shank 204 via thigh brace 206 and shank brace 208. In various embodiments, exoskeleton thigh 212 is rotatably coupled to exoskeleton trunk 216. In additional embodiments, exoskeleton thigh 212 is coupled to exoskeleton trunk 216 by more than one rotary joints. As discussed above, any suitable coupling may be implemented with components of the exoskeleton such that thigh link 102 and shank link 104 move with person's thigh 202 and person's shank 204.

Figure 28:
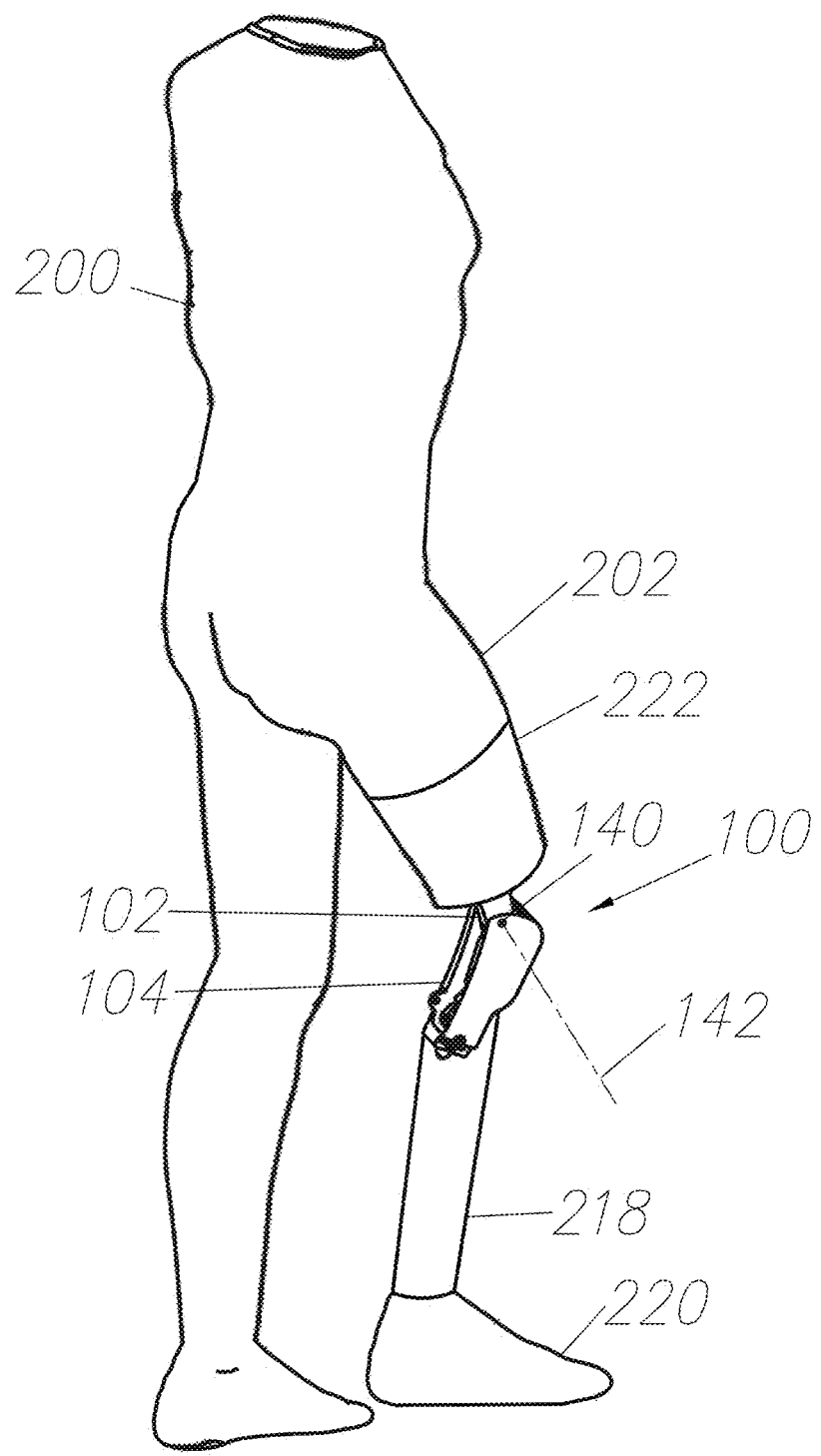
FIG. 28 shows an embodiment of artificial knee 100 worn by person 200 as a prosthetics knee, configured in accordance with various embodiments.

FIG. 28 shows an embodiment of artificial knee 100 worn by person 200 as a prosthetics knee, configured in accordance with various embodiments. In various embodiments, thigh link 102 couples with a person's thigh 202 via socket 222. As discussed above, any suitable coupling mechanism may be utilized to cause thigh link 102 to move in unison with person's thigh 202. In some embodiments, shank link 104 couples to an artificial shank 218. In various embodiments, artificial shank 218 further couples to artificial foot 220. In additional embodiments, artificial shank 218 includes a leaf spring that is design to contact with the ground with a designated amount of compliancy. Any suitable implementation of artificial shank 218 may be utilized with the above disclosed embodiments.

Figure 29A:
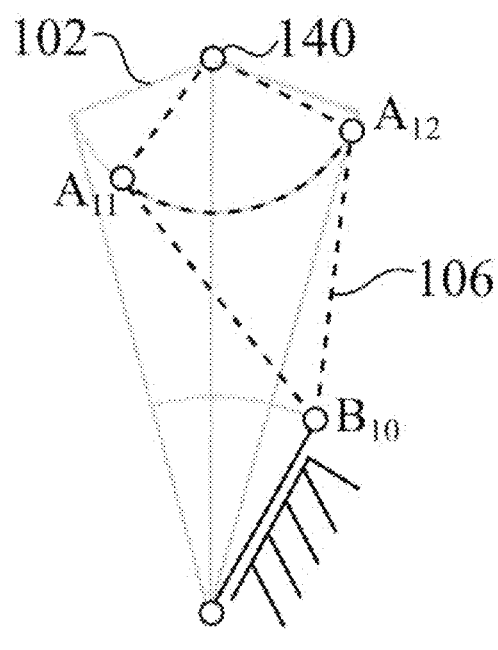
FIG. 29A and FIG. 29B depict adjustment mechanism 132 changing a distance between joint C 141 and knee joint 140, configured in accordance with various embodiments.
Figure 29B:
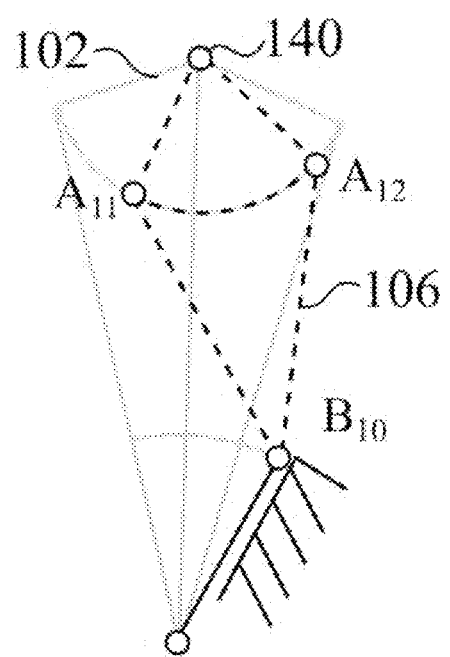

FIG. 29A and FIG. 29B depict adjustment mechanism 132 changing a distance between joint C 141 and knee joint 140, configured in accordance with various embodiments. As discussed above, engagement angle $\theta_{ENG}$ 802 and release angle $\theta_{REL}$ 806 can also be adjusted. FIG. 29B depicts a configuration when adjuster 110 has been moved along direction 606 (shown in FIG. 14). In this way, a length of shank link 104 (ground link) is increase from FIG. 29A to FIG. 29B. As shown in FIG. 29A and FIG. 29B, the difference between release angle $\theta_{REL}$ 806 (at which thigh link is at $A_{12}$) and engagement angle $\theta_{ENG}$ 802 (at which thigh link is at $A_{11}$) becomes smaller.

What is claimed is:

1. An artificial knee configured to be worn by a person during a walking cycle, the artificial knee comprising:
   a thigh link configured to move in unison with a thigh of the person;
   a shank link rotatably coupled to the thigh link,
      wherein knee extension motion is straightening of the artificial knee, and
      wherein knee flexion motion is bending of the artificial knee opposite of the knee extension motion; and
   a compression spring rotatably coupled to the thigh link at a first end of the compression spring, the compression spring coupled to the shank link at a second end of the compression spring,
   wherein during a first phase of the walking cycle, the compression spring provides a torque between the thigh link and the shank link that resists knee flexion motion of the shank link relative to the thigh link,
   wherein during a second phase of the walking cycle, the compression spring provides a torque between the thigh link and the shank link that encourages knee flexion motion of the shank link relative to the thigh link,
   wherein the artificial knee further comprises:
      a follower link, wherein the compression spring is coupled to the shank link at the second end via the follower link such that the thigh link, the shank link, the follower link, and the compression spring form a four bar linkage having rotary joints, and
      a constraint configured to constrain a motion of the follower link relative to the shank link during the first phase of the walking cycle and the second phase of the walking cycle,
   wherein the first phase of the walking cycle corresponds to a phase of the walking cycle in which an angle of the artificial knee is between an engagement angle and a toggle angle, wherein the second phase of the walking cycle corresponds to a phase of the walking cycle in which the angle of the artificial knee is between the toggle angle and a release angle, wherein the engagement angle is greater than a minimum angle of the artificial knee during the walking cycle but less than a maximum angle of the artificial knee during a stance phase of the walking cycle, wherein the toggle angle is greater than the maximum angle of the artificial knee during the stance phase of the walking cycle but less than an angle of the artificial knee at a toe off point of the walking cycle, and wherein the release angle is greater than the angle of the artificial knee at the toe off point of the walking cycle but less than a maximum angle of the artificial knee during the walking cycle.

2. The artificial knee of claim 1, wherein the compression spring generates a force that passes through a coupling location of the thigh link relative to the shank link during a stance phase of the walking cycle.

3. The artificial knee of claim 1, wherein the shank link is configured to move in unison with the shank of the person.

4. The artificial knee of claim 1, wherein the compression spring generates a force that passes through a coupling location of the thigh link relative to the shank link during a knee flexion motion of the thigh link relative to the shank link.

5. The artificial knee of claim 1, wherein the constraint is configured to block the motion of the follower link near a singular point, wherein the singular point is a point where the compression spring and the follower link are in line with each other.

6. An artificial knee configured to be worn by a person during a walking cycle, the artificial knee comprising:
- a thigh link configured to move in unison with a thigh of the person;
- a shank link configured to move in unison with a shank of the person, the shank link being rotatably coupled to the thigh link,
  - wherein knee extension motion is straightening of the artificial knee, and
  - wherein knee flexion motion is bending of the artificial knee opposite of the knee extension motion;
- a compression spring rotatably coupled to the thigh link at a first end of the compression spring;
- a follower link rotatably coupled to a second end of the compression spring from a first end of the follower link, the follower link being rotatably coupled to the shank link from a second end of the follower link such that the thigh link, the shank link, the follower link, and the compression spring form a four bar linkage; and
- a constraint configured to constrain a motion of the follower link relative to the shank link during a first phase of the walking cycle and a second phase of the walking cycle,
- wherein during the first phase of the walking cycle, the constraint constrains the motion of the follower link such that the compression spring provides a torque between the thigh link and the shank link that resists knee flexion motion of the shank link relative to the thigh link,
- wherein during the second phase of the walking cycle, the constraint constrains the motion of the follower link such that the compression spring provides a torque between the thigh link and the shank link that encourages knee flexion motion of the shank link relative to the thigh link, and
- wherein the first phase of the walking cycle corresponds to a phase of the walking cycle in which an angle of the artificial knee is between an engagement angle and a toggle angle, wherein the second phase of the walking cycle corresponds to a phase of the walking cycle in which the angle of the artificial knee is between the toggle angle and a release angle, wherein the engagement angle is greater than a minimum angle of the artificial knee during the walking cycle but less than a maximum angle of the artificial knee during a stance phase of the walking cycle, wherein the toggle angle is greater than the maximum angle of the artificial knee during the stance phase of the walking cycle but less than an angle of the artificial knee at a toe off point of the walking cycle, and wherein the release angle is greater than the angle of the artificial knee at the toe off point of the walking cycle but less than a maximum angle of the artificial knee during the walking cycle.

7. The artificial knee of claim 6, wherein the constraint is configured to block the motion of the follower link near a singular point.

8. The artificial knee of claim 7, wherein the singular point is a point where the compression spring and the follower link are in line with each other.

9. An artificial knee configured to be worn by a person during a walking cycle, the artificial knee comprising:
- a thigh link configured to move in unison with a thigh of the person;
- a shank link configured to move in unison with a shank of the person, the shank link being rotatably coupled to the thigh link,
  - wherein knee extension motion is straightening of the artificial knee, and
  - wherein knee flexion motion is bending of the artificial knee opposite of the knee extension motion;
- a compression spring rotatably coupled to the thigh link from a first end of the compression spring, the compression spring being rotatably coupled to the shank link from a second end of the compression spring; and
- a constraint configured to constrain a motion of a follower link relative to the shank link during a first phase of the walking cycle and a second phase of the walking cycle,
- wherein when the follower link is moved from a singular point toward the constraint, the constraint constrains a motion of the follower link, and the compression spring provides a torque between the thigh link and the shank link that resists knee flexion motion of the shank link relative to the thigh link,
- wherein when the follower link is moved from the singular point away from the constraint, the constraint does not constrain the motion of the follower link, and knee flexion motion and knee extension motion of the thigh link relative to the shank link is unimpeded, and
- wherein when the follower link is moved from the singular point away from the constraint, the constraint does not constrain the motion of the follower link, and knee flexion motion and knee extension motion of the thigh link relative to the shank link is unimpeded,
- wherein the first phase of the walking cycle corresponds to a phase of the walking cycle in which an angle of the artificial knee is between an engagement angle and a toggle angle, wherein the second phase of the walking cycle corresponds to a phase of the walking cycle in which the angle of the artificial knee is between the toggle angle and a release angle, wherein the engagement angle is greater than a minimum angle of the artificial knee during the walking cycle but less than a maximum angle of the artificial knee during a stance phase of the walking cycle, wherein the toggle angle is greater than the maximum angle of the artificial knee during the stance phase of the walking cycle but less than an angle of the artificial knee at a toe off point of the walking cycle, and wherein the release angle is greater than the angle of the artificial knee at the toe off point of the walking cycle but less than a maximum angle of the artificial knee during the walking cycle.

10. The artificial knee of claim 9 further comprising:
a leaf spring configured to move the follower link from the singular point away from the constraint.

11. An artificial knee configured to be worn by a person during a walking cycle, the artificial knee comprising:
- a thigh link configured to move in unison with a thigh of the person;
- a shank link configured to move in unison with a shank of the person, the shank link being rotatably coupled to the thigh link,
  - wherein knee extension motion is straightening of the artificial knee, and
  - wherein knee flexion motion is bending of the artificial knee opposite of the knee extension motion;
- a compression spring rotatably coupled to the thigh link from a first end of the compression spring, the compression spring being rotatably coupled to the shank link from a second end of the compression spring,
  - wherein during a first phase of the walking cycle, the compression spring provides a torque between the thigh link and the shank link that resists knee flexion motion of the shank link relative to the thigh link, and wherein during a second phase of the walking cycle, the compression spring provides a torque between the thigh link and the shank link that encourages knee flexion motion of the shank link relative to the thigh link;

a follower link rotatably coupled to the second end of the compression spring from a first end of the follower link, the follower link being rotatably coupled to the shank link from a second end of the follower link such that the thigh link, the shank link, the follower link, and the compression spring form a four bar linkage; and a constraint configured to constrain a motion of the follower link relative to the shank link near a singular point, wherein the singular point is a point where the compression spring and the follower link are in line with each other, wherein when the follower link is moved from the singular point toward the constraint, the constraint constrains the follower link, and the compression spring generates a force such that the force passes through a joint of the artificial knee during the first phase and second phase of the walking cycle, wherein when the follower link is moved from the singular point toward the constraint, the constraint constrains the follower link, and the compression spring generates a force such that the force passes through a joint of the artificial knee during the first phase and second phase of the walking cycle, wherein the first phase of the walking cycle corresponds to a phase of the walking cycle in which an angle of the artificial knee is between an engagement angle and a toggle angle, wherein the second phase of the walking cycle corresponds to a phase of the walking cycle in which the angle of the artificial knee is between the toggle angle and a release angle, wherein the engagement angle is greater than a minimum angle of the artificial knee during the walking cycle but less than a maximum angle of the artificial knee during a stance phase of the walking cycle, wherein the toggle angle is greater than the maximum angle of the artificial knee during the stance phase of the walking cycle but less than an angle of the artificial knee at a toe off point of the walking cycle, and wherein the release angle is greater than the angle of the artificial knee at the toe off point of the walking cycle but less than a maximum angle of the artificial knee during the walking cycle.

12. The artificial knee of claim 11 further comprising:
a leaf spring configured to move the follower link from the singular point away from the constraint.

13. The artificial knee of claim 1, wherein at least a portion of the first phase of the walking cycle occurs during the stance phase of the walking cycle, and wherein at least a portion of the second phase of the walking cycle occurs during the stance phase of the walking cycle.

14. The artificial knee of claim 1, wherein at least a portion of the first phase of the walking cycle occurs during the stance phase of the walking cycle, and wherein at least a portion of the second phase of the walking cycle occurs during a swing phase of the walking cycle.

15. The artificial knee of claim 1, wherein during a third phase of the walking cycle, the compression spring does not provide a torque between the thigh link and the shank link.

16. The artificial knee of claim 15, wherein at least a portion of the first phase of the walking cycle occurs during the stance phase of the walking cycle, wherein at least a portion of the second phase of the walking cycle occurs during a swing flexion phase of the walking cycle, and wherein at least a portion of the third phase of the walking cycle occurs during a swing extension phase of the walking cycle.

17. The artificial knee of claim 1, wherein the engagement angle is greater than 0 degrees but less than 20 degrees, wherein the toggle angle is greater than 20 degrees but less than 35 degrees, and wherein the release angle is greater than 35 degrees but less than 65 degrees.

18. The artificial knee of claim 1, wherein the engagement angle is approximately 5 degrees, wherein the toggle angle is approximately 30 degrees, and wherein the release angle is approximately 55 degrees.

* * * * *